US009598721B2

(12) United States Patent
Klein et al.

(10) Patent No.: US 9,598,721 B2
(45) Date of Patent: Mar. 21, 2017

(54) UNIVERSALLY APPLICABLE LYSIS BUFFER AND PROCESSING METHODS FOR THE LYSIS OF BODILY SAMPLES

(75) Inventors: Matthias Klein, Böblingen (DE); Gerd Lüdke, Holzgerlingen (DE); Andreas Boos, Bondorf (DE)

(73) Assignee: Curetis GmbH, Holzgerlingen (DE)

( * ) Notice: Subject to any disclaimer, the term of this patent is extended or adjusted under 35 U.S.C. 154(b) by 901 days.

(21) Appl. No.: 13/698,216

(22) PCT Filed: May 9, 2011

(86) PCT No.: PCT/EP2011/002303
§ 371 (c)(1),
(2), (4) Date: Nov. 15, 2012

(87) PCT Pub. No.: WO2011/144304
PCT Pub. Date: Nov. 24, 2011

(65) Prior Publication Data
US 2013/0065223 A1    Mar. 14, 2013

(30) Foreign Application Priority Data
May 17, 2010    (EP) .................................... 10005128

(51) Int. Cl.
*C12Q 1/68*     (2006.01)
*C12N 15/10*    (2006.01)
(52) U.S. Cl.
CPC ....... *C12Q 1/6806* (2013.01); *C12N 15/1006* (2013.01)
(58) Field of Classification Search
None
See application file for complete search history.

(56) References Cited

U.S. PATENT DOCUMENTS 7,482,116 B2    1/2009  Birnboim
2003/0215845 A1   11/2003  Bille
(Continued)

FOREIGN PATENT DOCUMENTS

IN    694/KOL/2007 A    5/2007
JP    H02273197 A       11/1990
(Continued)

OTHER PUBLICATIONS

Koeplinger KA et al: "Caspase 8: An Efficient Method for Large-Scale Autoactivation of Recombinant Procaspase 8 by Matrix Adsorption and Characterization of the Active Enzyme", Protein Expression and Purification, Academic Press, San Diego, vol. 18, No. 3, (2000) pp. 378-387.
(Continued)

*Primary Examiner* — Samuel Woolwine
(74) *Attorney, Agent, or Firm* — Neal, Gerber & Eisenberg LLP; Kevin A. O'Connor, Esq.

(57) ABSTRACT

The present invention provides a universally applicable lysis buffer comprising a chaotropic 5 agent, a reducing agent, and a proteolytic enzyme suitable for processing a wide variety of different sample types, such as different types of bodily samples relevant for the diagnosis of a respiratory disease. Furthermore, the present invention provides the use of a chaotropic agent, a reducing agent, and a proteolytic enzyme for the lysis of a broad spectrum of bodily samples. Moreover, the present invention provides a method for processing bodily samples which is universally applicable to the lysis of a variety of different types of bodily samples. Furthermore, the present invention provides methods for analyzing a bodily sample or for detecting the presence of a pathogen in a bodily sample, preferably, for diagnosing a respiratory disease, such as pneumonia or tuberculosis. Preferably, these methods are universally applicable to a
(Continued)

variety of sample types, are applicable as one-tube-processes, are 15 suitable for performance in a high-throughput setting, and are automatable.

9 Claims, 16 Drawing Sheets

(56) References Cited

U.S. PATENT DOCUMENTS

| | | | |
|---|---|---|---|
| 2005/0019814 A1 | 1/2005 | Laugharn, Jr. et al. | |
| 2005/0114915 A1* | 5/2005 | Cohen et al. | 800/21 |
| 2007/0026435 A1* | 2/2007 | Templer | C12N 15/1013 435/6.11 |
| 2007/0160999 A1* | 7/2007 | Calabrese | 435/6 |
| 2007/0231793 A1* | 10/2007 | Karaolis | 435/6 |
| 2009/0054809 A1 | 2/2009 | Morishita et al. | |
| 2010/0129821 A1* | 5/2010 | Fredricks | C12Q 1/6895 435/6.15 |
| 2010/0161530 A1* | 6/2010 | Petritis et al. | 706/13 |

FOREIGN PATENT DOCUMENTS

| | | |
|---|---|---|
| JP | H10503655 A | 4/1998 |
| JP | 2002062299 A | 2/2002 |
| JP | 2003526361 A | 9/2003 |
| JP | 2004534731 A | 11/2004 |
| JP | 2005230012 A | 9/2005 |
| JP | 2008142083 A | 6/2008 |
| JP | 2008249700 A | 10/2008 |
| JP | 2008283891 A | 11/2008 |
| JP | 2008543286 A | 12/2008 |
| KR | 20090110969 A | 10/2009 |
| KR | 101003778 B1 | 12/2010 |
| NO | WO 2006109693 A1 | 10/2006 |
| WO | WO9604402 A1 | 2/1996 |
| WO | WO0168818 A2 | 9/2001 |
| WO | WO02056030 A2 | 7/2002 |
| WO | WO2004079333 A2 | 9/2004 |
| WO | WO2005010186 A1 | 2/2005 |
| WO | WO2006133399 A1 | 12/2006 |
| WO | WO2007133495 A1 | 11/2007 |

OTHER PUBLICATIONS

Singh RR & Chang JY: "Structural stability of human .alpha.-thrombin studied by disulfide reduction and scrambling", Biochimica Et Biophysica Acta, vol. 1651, (2003) pp. 85-92.

Xiang X et al: "Comparison of different methods of total RNA extraction for viral detection in sputum", Journal of Virological Methods, vol. 94, No. 1-2, (2001) pp. 129-135.

International Search Report and Written Opinion of the International Searching Authority for International Patent Application No. PCT/EP2011/002303, mailed on Jun. 1, 2011.

Extended European Search Report for European Patent Application No. 10005128.3, dated Sep. 28, 2010.

Tarhan, et al., "Evaluation of the Efficacy of Five DNA Extraction Methods for the Detection of Mycobacterium tuberculosis DNA in Direct and Processed Sputum by an In-House PCR Method," Turkish Journal of Medical Sciences, 2009, 39(2), pp. 253-257.

Kolk, et al., "Detection of Mycobacterium tuberculosis in Clinical Samples by Using Polymerase Chain Reaction and a Nonradioactive Detection System," Journal of Clinical Microbiology, 1992, 30(10), pp. 2567-2575.

Ju-Ock, et al., "Comparison of Various DNA Extraction Methods for Diagnosis of Tuberculosis Using a Polymerase Chain Reaction," Tuberculosis and Respiratory Diseases, 1993, vol. 40, No. 1, pp. 43-51.

Martinetti, "Studio Sulla Fluidificazione ed Omogeneizzazione Dell'escreato," Annali Sclavo; rivista di microbiologia e di immunologia, 1976, vol. 18, No. 2, pp. 156-164. (English abstract).

* cited by examiner

FIGURE 4

| | viscosity | blood | sediment | impact on lysis | | | performance (full protocol) | |
| --- | --- | --- | --- | --- | --- | --- | --- | --- |
| | | | | ProtK | 96°C | milling | lysis | silica membrane |
| sputum | +++ | + | + | (+) | + | +++ | OK | OK |
| tracheal secretion | ++ | o | +++ | ++ | ++ | + | slightly turbid | slight colorization |
| tracheal secretion | + | ++ | ++ | o | o | o | OK | OK |
| bronchic secretion | ++ | o | ++ | + | + | o | OK | OK |
| BAL | o | + | + | o | o | o | OK | OK |
| gastric juice | o | o | ++ | o | o | o | OK | OK |
| pleural punctate | o | + | + | o | o | o | OK | OK |
| punctate/blood | + | +++ | +++ | o | ++ | + | OK | slight colorization |
| punctate | + | + | o | o | o | o | OK | OK |
| drainage | + | +++ | +++ | o | o | o | OK | slight colorization |
| drainage | + | + | ++ | o | o | o | OK | OK |
| blood | n.a. | n.a. | n.a. | ++ | o | o | OK | OK |

FIGURE 11

| | | PCR 1 | | | PCR 2 | | | | |
|---|---|---|---|---|---|---|---|---|---|
| | | K. pneum. | Str. pn. | P. aer. | S. aur. | Haem. | E. coli | Str. species | |
| sputum | 1 | o | ■ | o | o | ■ | o | ■ | S. pneumoniae |
| | 2 | ++ | o | o | (+) | ■ | o | ++ | K. pneum., S. pneum., Haem. |
| | 3 | o | o | o | ++ | o | + | + | S. aureus, E. coli |
| | 4 | o | o | o | o | o | (+) | ■ | S. pneumoniae |
| | 5 | o | o | o | o | o | o | ++ | S. pneumoniae |
| | 6 | o | ■ | o | o | o | o | ++ | negative |
| tracheal secretion | 1 | o | o | o | o | o | o | + | negative |
| | 2 | o | + | o | o | + | o | ++ | S. pneum., Haem., E. coli |
| | 3 | o | + | o | o | (+) | ++ | ++ | S. pneumoniae, E. coli |
| | 4 | o | (+) | o | o | (+) | o | + | negative |
| | 5 | o | o | o | o | o | (+) | + | negative |
| | 6 | o | ++ | o | o | ++ | o | ++ | S. pneumoniae, Haem. |
| bronchial secretion | 1 | o | o | o | o | o | + | + | E. coli |
| | 2 | o | o | o | + | o | (+) | + | S. aureus |
| | 3 | o | ++ | o | o | ++ | o | ++ | S. pneumoniae, Haem. |
| | 4 | o | o | o | o | o | o | (+) | negative |
| BAL | 1 | o | o | ++ | o | o | o | ++ | P. aeruginosa |
| | 2 | o | o | o | o | o | (+) | ++ | negative |
| | 3 | o | ++ | o | o | + | o | + | S. pneumoniae, Haem. |
| | 4 | o | o | o | o | o | (+) | o | negative |
| | 5 | o | ++ | o | o | + | (+) | ++ | S. pneumoniae, Haem. |
| gastric juice | 1 | o | ++ | o | + | ++ | o | ++ | S. pneum., S. aureus, Haem. |
| | 2 | o | o | ++ | o | o | o | ++ | P. aeruginosa |
| | 3 | o | (+) | o | o | ++ | o | ++ | negative |
| | 4 | o | ++ | o | o | ++ | o | ++ | S. pneumoniae, Haem. |
| pleural punctate | 1 | o | o | o | o | o | o | o | negative |
| | 2 | o | o | o | o | o | o | o | negative |

■ > 100 nM    □ 10-100 nM    + 1-10 nM    (+) < 1 nM (counted as "negative")

UNIVERSALLY APPLICABLE LYSIS BUFFER AND PROCESSING METHODS FOR THE LYSIS OF BODILY SAMPLES

CROSS REFERENCE TO RELATED APPLICATIONS

This application is a national stage application of PCT/EP2011/002303, which was filed on May 9, 2011, and which claims priority to and benefit of European Application No. 10 005 128.3, filed May 17, 2010. The contents of the above-identified applications are incorporated by reference in their entireties.

TECHNICAL FIELD OF THE INVENTION

The invention relates to a universally applicable lysis buffer and processing method for the lysis of bodily samples, in particular bodily samples that are relevant for the diagnosis of respiratory diseases.

BACKGROUND OF THE INVENTION

Molecular techniques, in particular analyses of nucleic acids, gain more and more importance in the field of diagnostics. In particular, the molecular diagnostics in the field of respiratory diseases, such as pneumonia or tuberculosis, often require the analysis of bodily samples such as body fluids which are very diverse in their appearance, e.g., blood, sputum, and tracheal secretions. To date, each sample type requires a different lysis buffer, processing method, and lysis procedure which are often not transferable to other sample types. No protocol has been published so far which covers all sample types relevant for molecular diagnostics of respiratory diseases, e.g., pneumonia. Thus, it is currently not possible to use a standardized, user-friendly routine protocol for all sample types relevant for diagnosis of pneumonia patients. Thus, lysis buffers and processing methods which are universally applicable to a wide variety of bodily samples, in particular, samples which are relevant for the diagnosis of respiratory diseases, such as pneumonia, are desired.

It is particularly important for patients with severe acute infections of the respiratory tract to rapidly identify causative pathogens and concomitant risk factors, such as drug resistances, to enable a switch from the initial broad-band antibiotic therapy to a customized therapy specifically targeting causative pathogens with their identified drug resistances. International guidelines for severe pneumonia subtypes, such as hospital-acquired, ventilator-acquired, or healthcare-associated pneumonia, strongly recommend identification of certain risk pathogens (e.g., *Pseudomonas aeruginosa*) or risk factors for multi-drug resistances (e.g., mecA) which have a significant impact on the design of the antibiotic regimen.

The diagnostic approaches used to date for respiratory diseases, e.g., chest radiography, smear microscopy, physical examination, or microbial culture tests, e.g., of sputum cultures, cultures of bronchoscopic samples, or blood cultures, are often not suitable to identify pathogens or risk factors and/or have very low efficiencies. Thus, to date, there is no efficient detection method which is supported by validated clinical studies for the diagnosis of pneumonia. As a consequence, pneumonia guidelines do not recommend any diagnostic approach as a gold-standard method. Rather, a combination of different diagnostic methods covering different samples is used based on the expertise and experience of the attending physician. In this context, several respiratory as well as non-respiratory samples are used for the diagnosis. For example, blood cultures are used as indicators for bacteraemia or pleural punctates as indicators for empyema which leads to a high risk for mortality for pneumonia patients.

Samples which are relevant for the diagnosis of respiratory diseases are generally difficult to handle. Such samples encompass sputum, pus, pleural fluid, gastric aspirate, endotracheal aspirate, transtracheal aspirate, bronchoalveolar lavage, laryngeal swab, nasopharyngeal swabs, and others which are usually inhomogeneous mixtures of many different components of different chemical and physical behavior. Generally, such samples are highly viscous and even samples of the same type differ vastly in their composition. However, accessibility and lysis of inflammatory pathogens can be less efficient if they are trapped in a solid and viscous environment.

All diagnostic methods used so far aiming at detection of pathogens in samples of the respiratory tract require laborious sample processing for decontamination and liquefaction using a combination of enzymes such as proteases, lipases, DNases, or glycosidases, detergents, chaotropic agents, chelating agents, and reducing agents among others. However, some of these agents such as SDS are known inhibitors of nucleic acid amplification and analysis methods. Furthermore, due to the high infection risk any treatment of tuberculosis suspected samples requires an S3 environment with certified laminar flows and extensive protection measures to exclude any exposure of personnel to live bacteria. Thus, for molecular tests it would be of advantage to use bodily samples directly for nucleic acid diagnostics and circumvent the handling intensive decontamination and liquefaction procedures.

Thus, molecular diagnostics in respiratory diseases is currently time-consuming, laborious, error-prone, and associated with a high risk of contamination. Furthermore, since each sample type requires a different handling procedure, processing in a high-throughput setting is not possible.

Therefore, it is the aim of the present invention to provide a lysis buffer and a simple processing method which are universally applicable for the lysis of a variety of different sample types, such as bodily samples relevant for the diagnosis of respiratory diseases, and which reduce the need for intensive handling of the samples, and thus, reduce the risk of contamination and allow for molecular diagnostics in a high-throughput setting.

The present inventors have surprisingly found that a lysis buffer containing as the only active ingredients a chaotropic agent, a reducing agent, and a protease is universally applicable for the lysis of bodily samples, in particular, of bodily samples that are relevant for the diagnosis of respiratory diseases. Thus, the lysis buffer according to the present invention is universally applicable, for example, for the lysis of gastric juices and sputum or tracheal secretion samples, which are highly different in their compositions.

Furthermore, the present inventors have developed a processing method, which is easy and safe to perform, universally applicable, automatable, applicable in a high-throughput setting, and which does not require any laborious and time-consuming decontamination or liquefaction pretreatments of the samples. In particular, the processing method of the present invention allows performing the complete lysis procedure of a bodily sample in a single reaction tube, without the need for centrifugation and sample transferring or pipetting steps, substantially reducing the required hands-on work and contamination risk. The lysate resulting from the processing method according to the present invention can be directly transferred to nucleic acid isolation procedures, for example, based on silica membranes, silica beads, or magnetic beads technology, without the need for further nucleic acid purification methods such as phenol-chloroform extraction or precipitation. Thus, the lysates are, for example, suitable for direct transfer to a QiaAmp™ DNA isolation column without significant clogging of the column, which was not expected, in particular, for the highly viscous samples of the respiratory tract.

SUMMARY OF THE INVENTION

In one aspect, the present invention provides a lysis buffer comprising (i) at least one chaotropic agent, (ii) at least one reducing agent, and (iii) at least one proteolytic enzyme. Preferably, the lysis buffer according to the invention further comprises beads. Preferably, the lysis buffer according to the present invention is universally applicable for the lysis of bodily samples, preferably such bodily samples that are relevant for the diagnosis of a respiratory disease.

In another aspect, the present invention provides a use of (i) at least one chaotropic agent, (ii) at least one reducing agent, and at least one proteolytic enzyme for the lysis of a broad spectrum of bodily samples.

In a further aspect, the present invention provides a method for processing a bodily sample comprising the step of (i) providing a mixture comprising the bodily sample to be processed, at least one chaotropic agent, at least one reducing agent, and at least one proteolytic enzyme. Preferably, step (i) comprises the steps (a) contacting the components of the mixture and (b) mixing the components of the mixture. Preferably, the method further comprises the step of (ii) heating the mixture to a first temperature, preferably to a temperature at which the proteolytic enzyme is active. Preferably, the method further comprises the step of (iii) heating the mixture to a second temperature, preferably to at least 80° C. Preferably, the method further comprises the step of (iv) bead milling the mixture. In a preferred embodiment, the bead milling step (iv) is performed parallel to the heating step (iii). In a preferred embodiment, steps (ii) to (iv), preferably steps (i)(b) to (iv) of the method according to the present invention, are performed in an automated process. In a preferred embodiment, the method further comprises the step of (v) isolating a nucleic acid from the mixture.

In another aspect, the present invention relates to a method for analyzing a bodily sample comprising processing the bodily sample according to the method of the present invention for processing a bodily sample and (vi) applying the mixture to a nucleic acid amplification/analysis method.

In a further aspect, the present invention provides a method for detecting the presence of a pathogen in a bodily sample comprising processing the bodily sample according to the method of the present invention for processing a bodily sample and (vi) applying the mixture to a nucleic acid amplification/analysis method that is suitable for detection of said pathogen. Preferably, said pathogen is associated with a respiratory disease.

In another aspect, the present invention provides a method for diagnosing a respiratory disease, such as pneumonia, tuberculosis, bronchitis, or pathogenic infections during cystic fibrosis or chronic obstructive pulmonary disease (COPD), or a respiratory tumor, in a subject comprising processing a bodily sample according to the method of the present invention for processing a bodily sample and (vi) applying the mixture to a method that is suitable for diagnosing the respiratory disease.

Preferably, the methods according to the present invention are universally applicable to different types of bodily samples, preferably to different types of bodily samples relevant for the diagnosis of a respiratory disease, and thus, the methods according to the present invention are preferably suitable to be applied in a high-throughput setting to a variety of different sample types.

In further aspects, the present invention provides a method for processing at least two bodily samples comprising processing each of the at least two bodily samples according to the method of the present invention for processing a bodily sample, wherein the at least two bodily samples are different types of bodily samples, a method for analyzing at least two bodily samples comprising analyzing each of the at least two bodily samples according to the method of the present invention for analyzing a bodily sample, wherein the at least two bodily samples are different types of bodily samples, and a method for detecting the presence of a pathogen in at least two bodily samples comprising detecting the presence of a pathogen in each of the at least two bodily samples according to the method of the present invention for detecting the presence of a pathogen, wherein the at least two bodily samples are different types of bodily samples.

In another aspect, the present invention provides a lysate of a bodily sample comprising a bodily sample, at least one chaotropic agent, at least one reducing agent, and at least one proteolytic enzyme.

In a further aspect, the present invention relates to a lysate obtainable by processing a bodily sample according to the method of the present invention for processing a bodily sample.

In another aspect, the present invention provides a kit comprising (i) a chaotropic agent, (ii) a reducing agent, (iii) a proteolytic enzyme, and (iv) an instruction leaflet. Preferably, the chaotropic agent and the reducing agent are provided in a composition in one or more reaction tubes, preferably screw cap tubes, which preferably also comprise beads, and preferably the proteolytic enzyme is provided separately from the chaotropic agent and the reducing agent, for example, in a separate tube, such as a storage tube, or as dried spot in the lid of the tube, preferably the screw cap tube, which preferably contains the composition comprising the chaotropic agent and the reducing agent. Preferably, the kit is universally applicable to the lysis of bodily samples, preferably to the lysis of bodily samples relevant for the diagnosis of a respiratory disease.

Process example A is a manual process using a standard vortex for mixing at 2500 rpm (standard maximum speed for an IKA vortex, devices from other suppliers might vary) for 30 sec (other times might work as well), pre-heated heating blocks and a milling device capable of a milling speed relating to approx. 100 g (other speeds might work as well, and speed may vary for other devices with different geometry). Note that for all milling/mixings steps the tubes are removed from the heating block and processed at room temperature.

Figure 2:
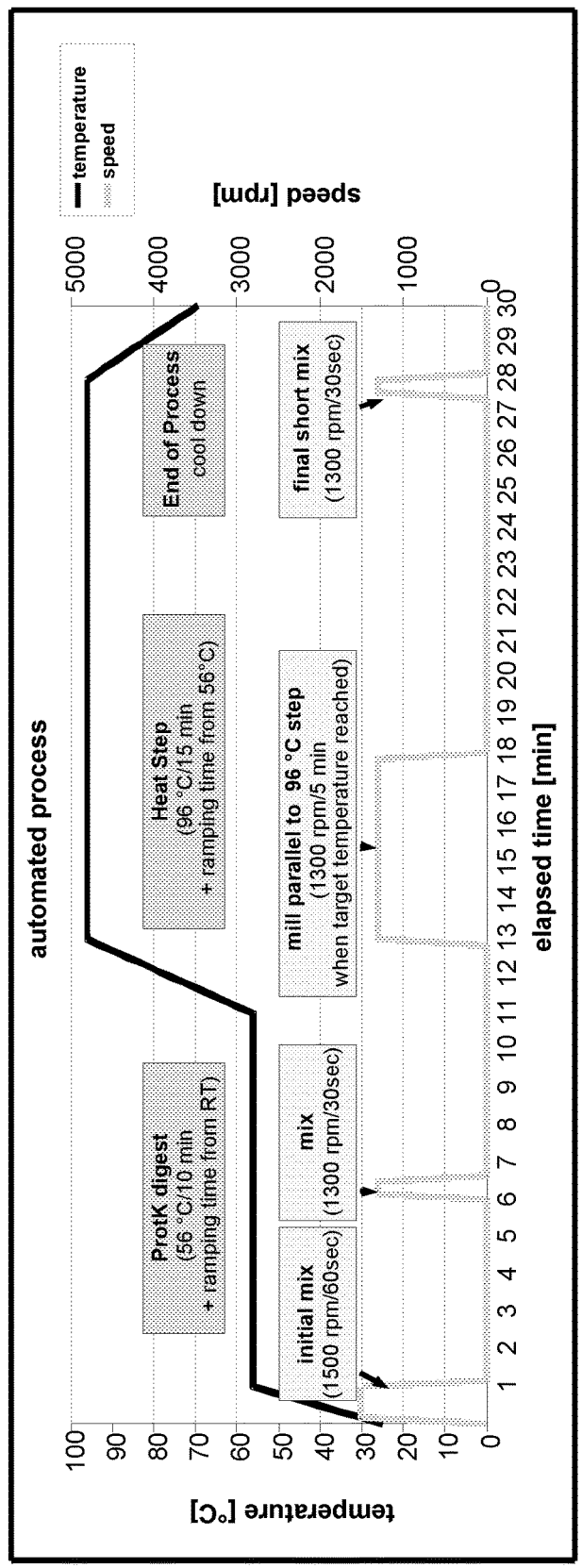

FIG. 2: Example for an automated lysis method using the lysis buffer according to the invention.

Process example B is an automated process using a bead milling device which performs all process steps (mixing, heating, milling). Milling speeds relate to forces between 50-100 g dependent on the device geometries. As the tubes are heated together with the chambers to the target temperatures, longer ramping rates are included in this example, still, ramping times are not critical and may also be considerably shorter.

Figure 3:
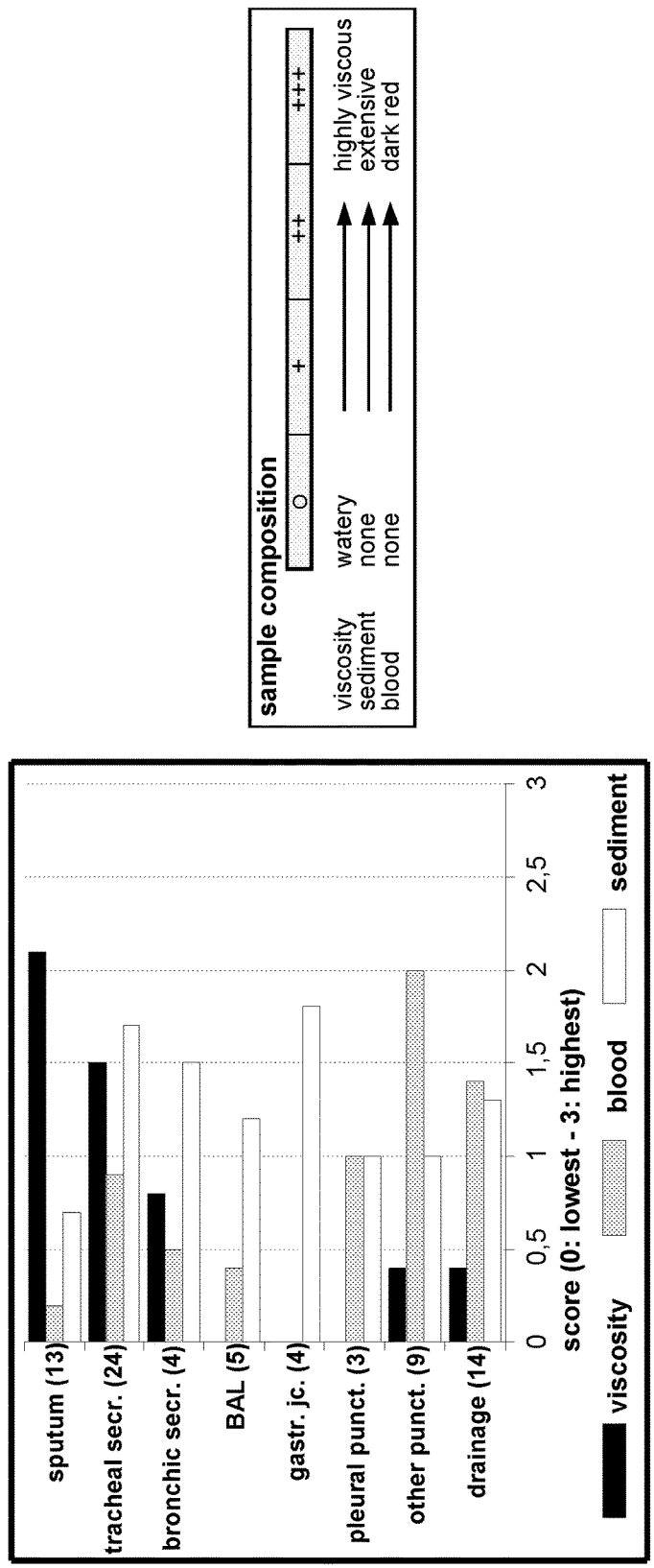

FIG. 3: Sample composition of different bodily sample types.

76 samples of different origins (respiratory and relevant other samples, like punctates and drainages) were scored for viscosity, blood, and sediment content to describe the differences of sample types based on an average score.

FIG. 4: Performance of lysis procedures with different bodily sample types.

Figure 1:
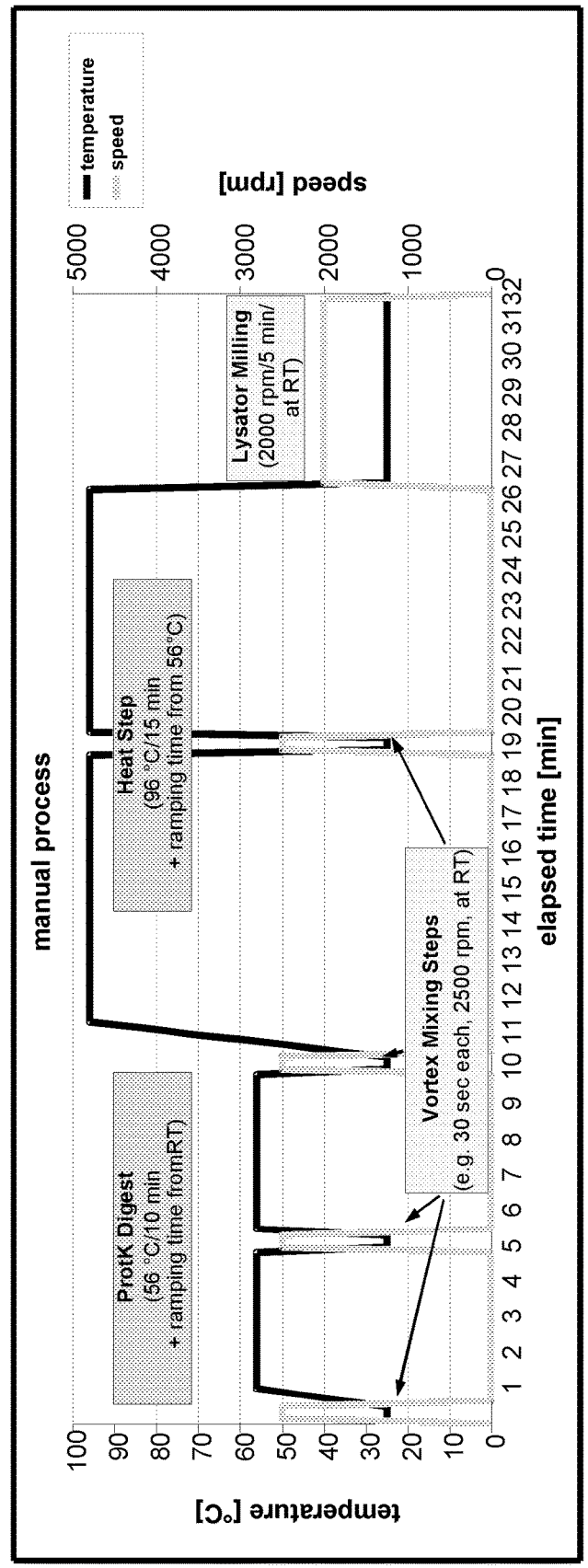
FIG. 1: Example for a manual lysis method using the lysis buffer according to the invention.

The number of samples processed for each sample type is given in brackets. From each sample type, including blood, reference samples were selected to cover the full range of relevant samples for respiratory diseases (total: 12 samples). Each of these samples was subjected to three different lysis protocols: (a) manual full lysis protocol as shown in FIG. 1 and described in Example 1 (full lysis protocol), (b) full lysis protocol without addition of proteinase K, (c) lysis protocol without second heating step (96° C.), instead samples were incubated at ambient temperature. All samples have been subjected to a final bead milling step of five minutes as described in Example 1 (full lysis protocol), the lysate was then transferred, mixed with ethanol and applied to a silica membrane column (QiaAmp™, Qiagen). Lysis efficiencies were scored after proteinase K digestion (first heating step), the second heating step (96° C.), and bead milling. In addition, turbidity of the supernatants was monitored. The flow-through after application of the lysate to the silica membranes was monitored using a centrifuge at reduced speed (4000 rpm instead of recommended 8000 rpm). The silica membrane was examined for coloring or remaining sample components which might indicate insufficient lysis.

Figure 5:
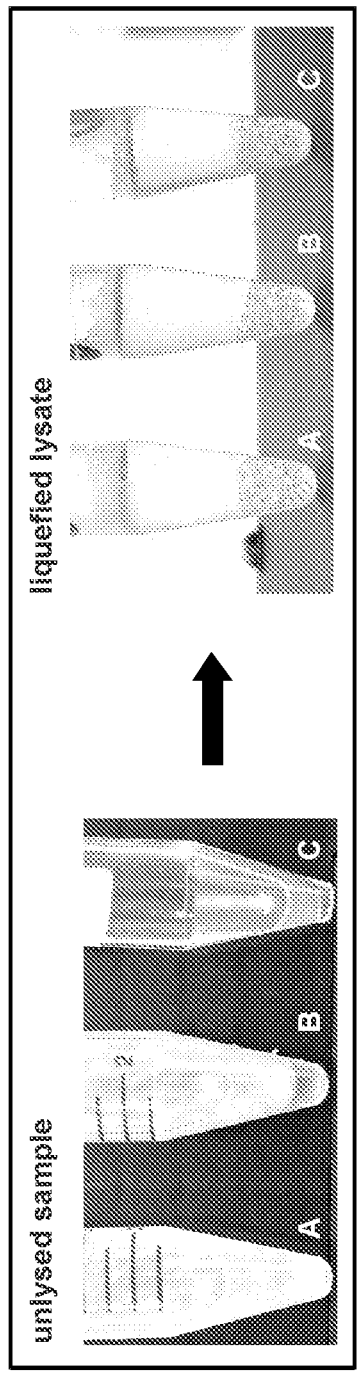

FIG. 5: Typical examples of patient samples lysed using the manual lysis method according to the present invention.

Lysed samples are also typical for the automated protocol.
A/B: sputa, C: tracheal secretion.

FIG. 6: Impact of bead milling and heating on the lysis of tracheal secretion samples (without proteinase K digest).

Figure 6A:
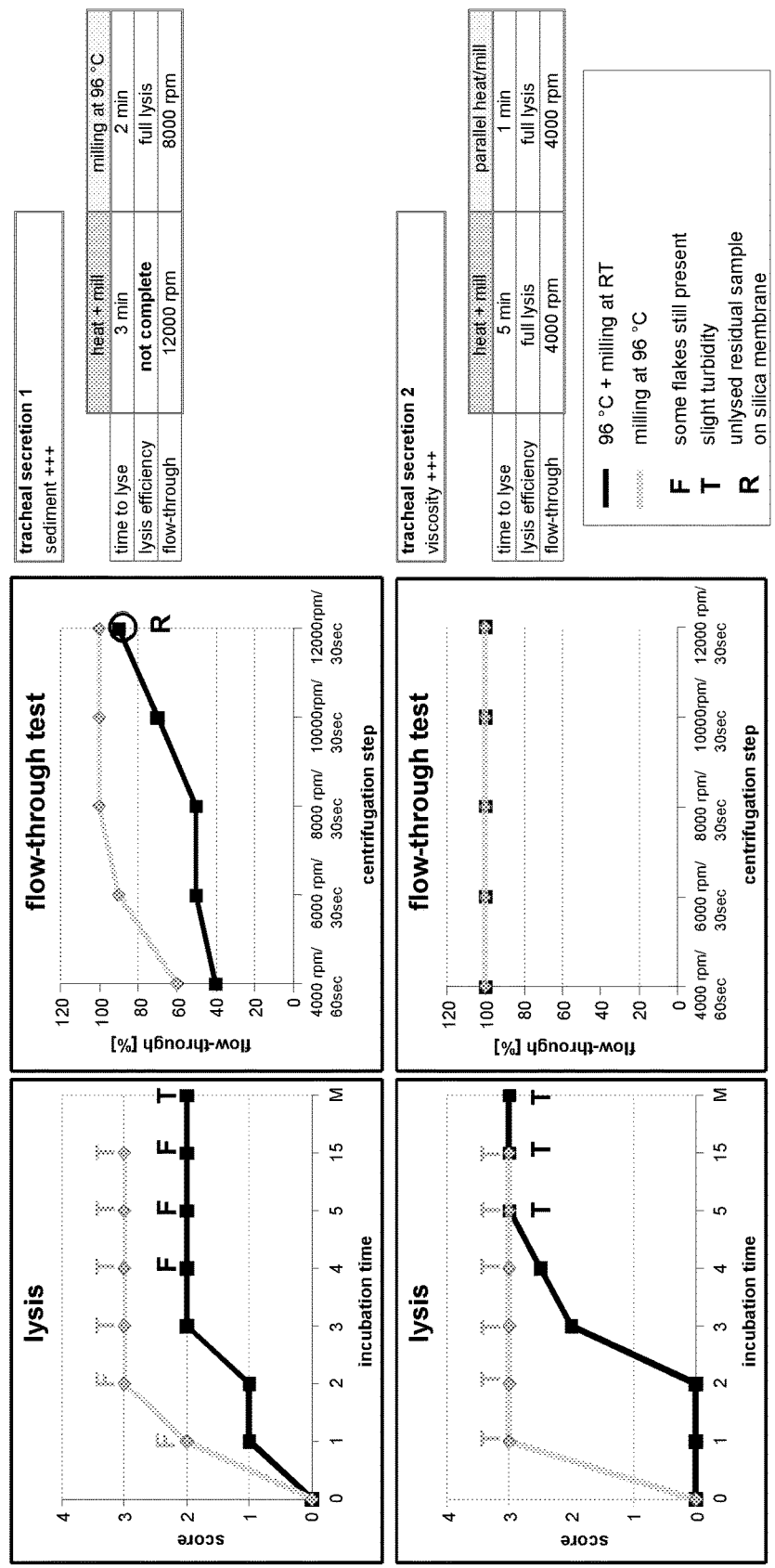
Figure 6B:
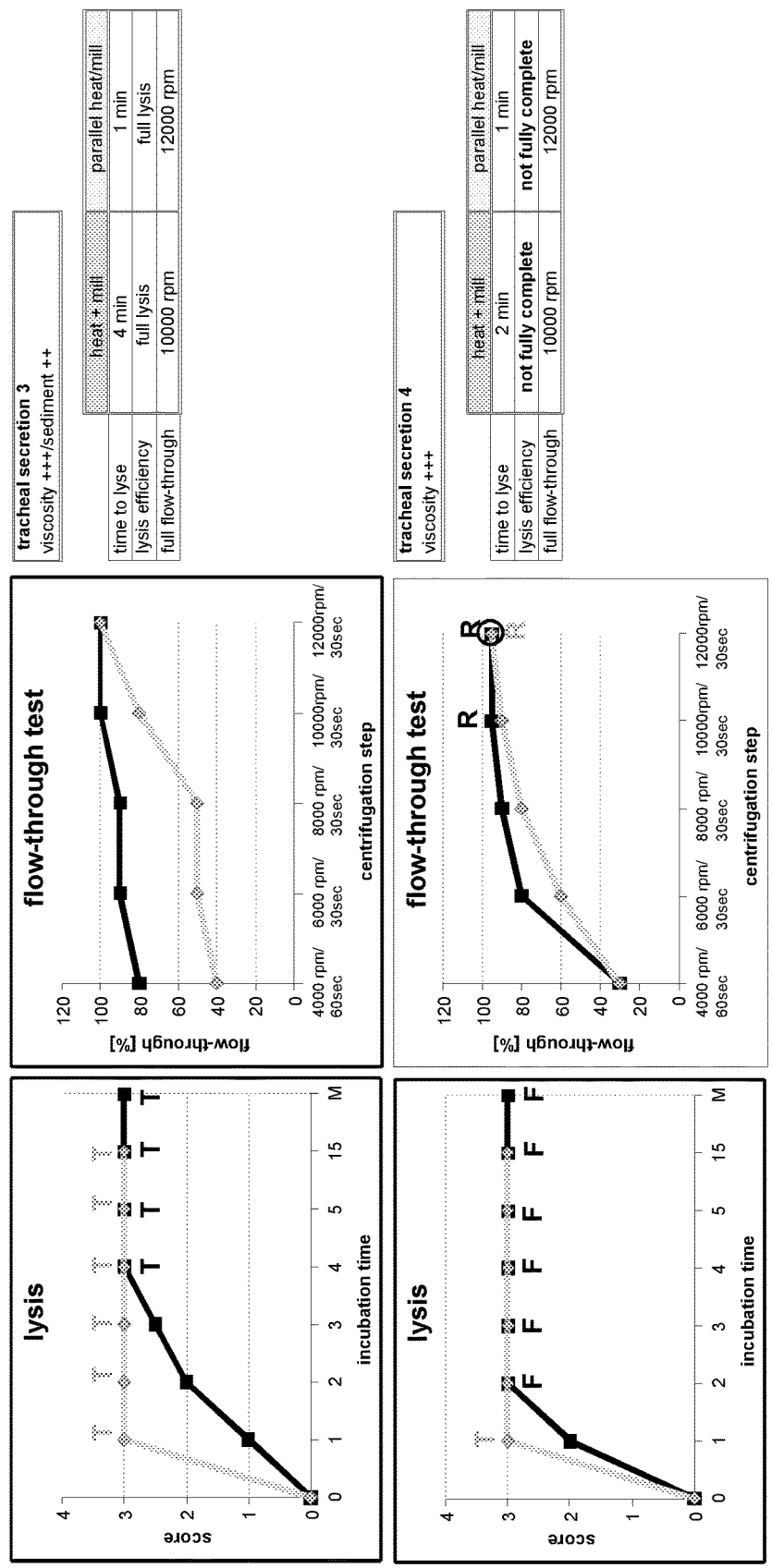

In a first step, samples were incubated at 96° C. for 15 minutes directly after addition of the lysis buffer and short mixing. Bead milling was performed for 5 minutes either during the heating step (96° C.) or at room temperature after completion of the 96° C. incubation step [M]. The progress of the lysis was monitored over time based on the lysis score (lysis score 0: not or only insufficiently lysed, mucous clumps still present; lysis score 1: partially lysed, minor clumps still present; lysis score 2: nearly completely lysed, still some unlysed bits present; lysis score 3: completely lysed). Lysed supernatants were applied to silica membranes essentially according to the manufacturer's instructions. Flow-through was monitored at increasing centrifugal forces starting at 4000 rpm. FIGS. 6A and 6B each show two examples of tracheal secretion samples reflecting the variability of samples of the same type.

FIG. 7: Impact of proteinase K digest on the lysis of tracheal secretion samples.

Figure 7A:
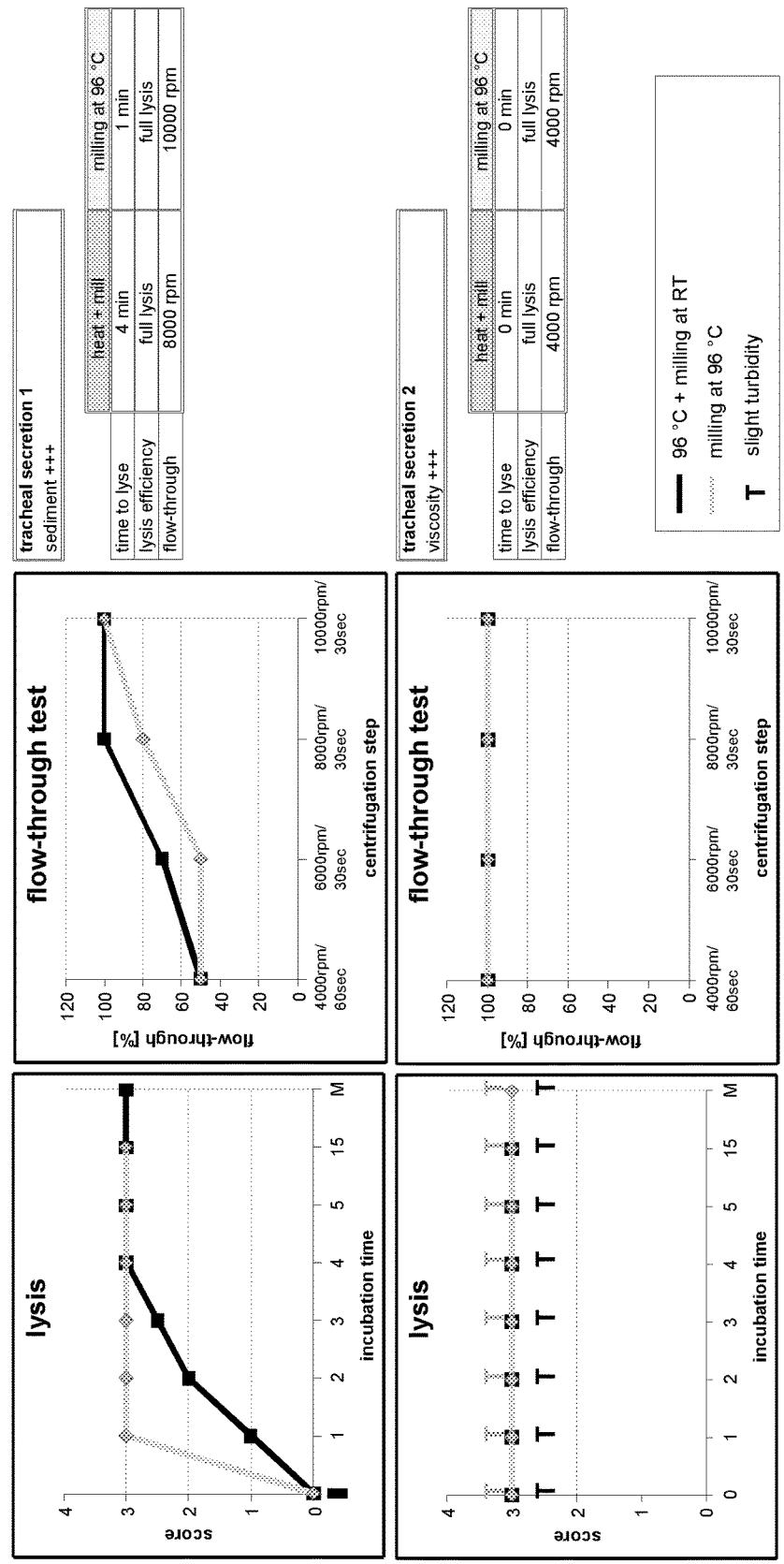
Figure 7B:
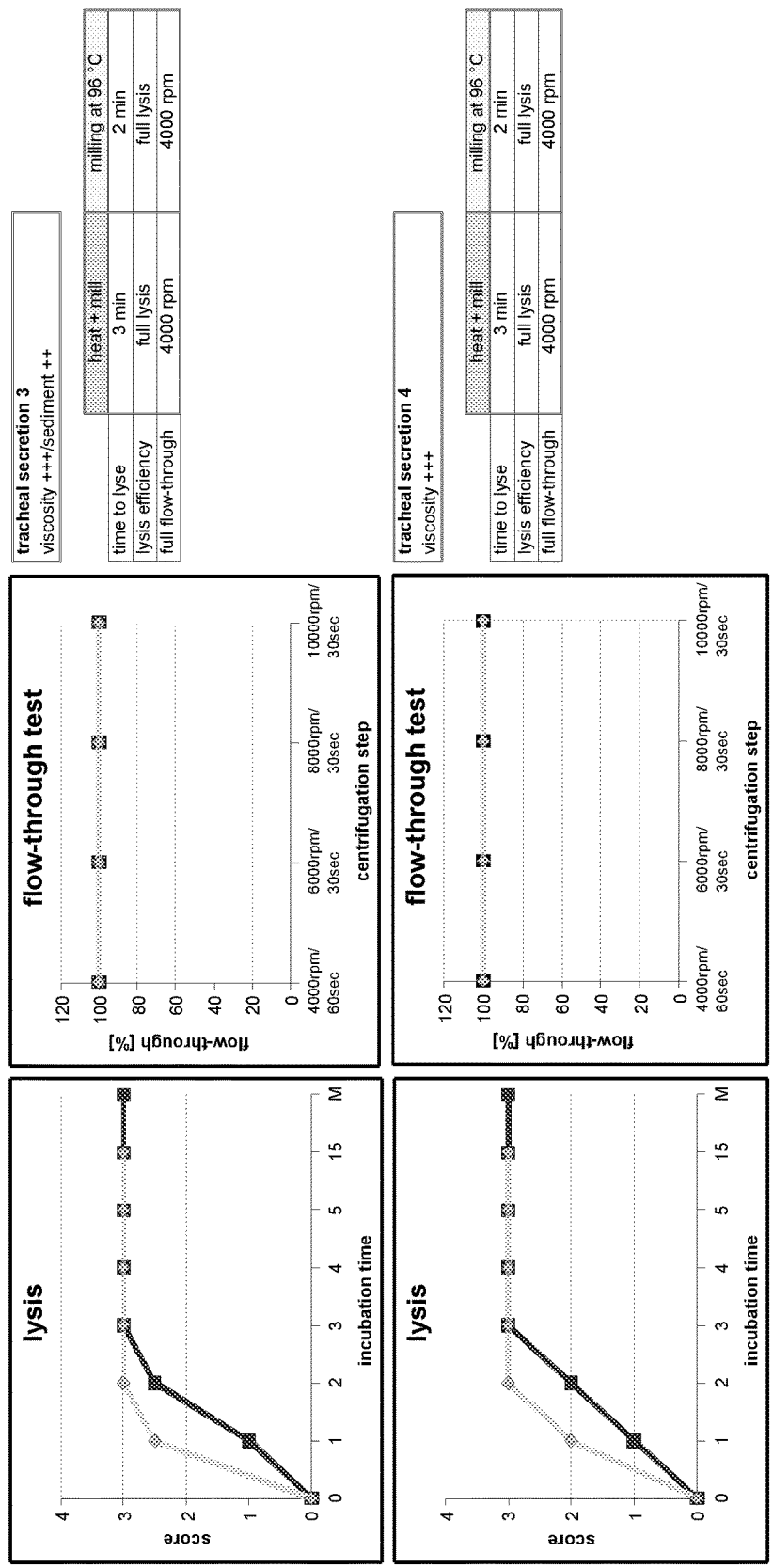

The lysis protocol was performed as described for FIG. 6 with the addition of a proteinase K digest before the heating step (96° C.) using the same sample as in FIG. 6. For the proteinase K digest, 20 µl Qiagen proteinase K (20 mg/ml) was added to the samples with lysis buffer and the samples were incubated at 56° C. for 10 minutes. Lysis efficiency was scored as described for FIG. 6. FIGS. 7A and 7B each show two examples of tracheal secretion samples.

Figure 8:
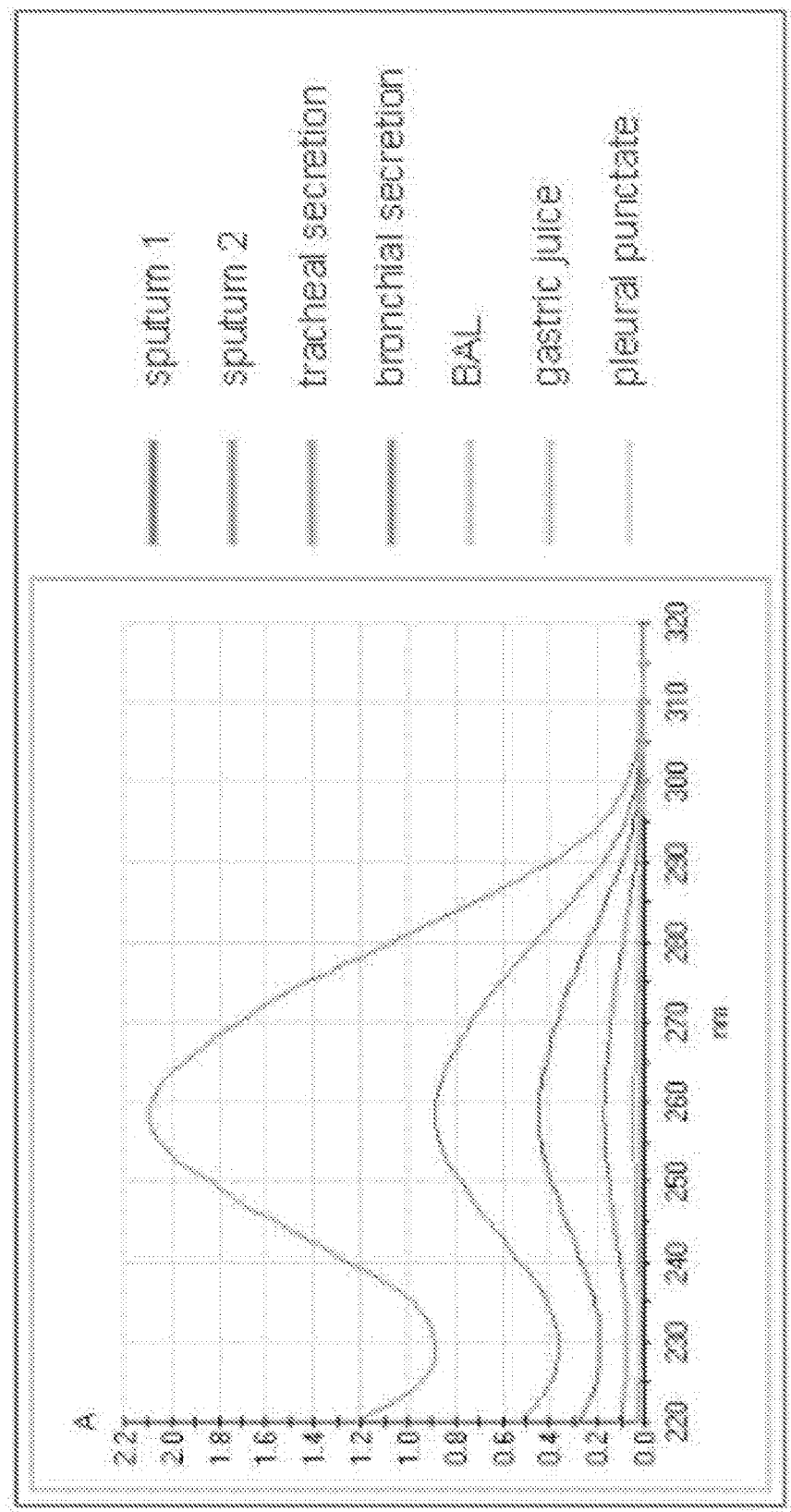

FIG. 8: DNA quality of purified DNAs from different bodily sample types.

Seven patient samples of different origins were spiked with *Pseudomonas aeruginosa* (20000 pathogens/ml=4400 pathogens/220 µl used sample) and lysed using the manual protocol as described in FIG. 1 and Example 1 (full lysis protocol). DNA was purified with the QiaAmp™ DNA Blood Kit using a centrifuge and eluted into 200 µl of water. The quality of isolated DNA purified from spiked samples was monitored by spectral analysis of the 5-fold diluted eluate (220-320 nm). BAL: bronchoalveolar lavage.

Figure 9:
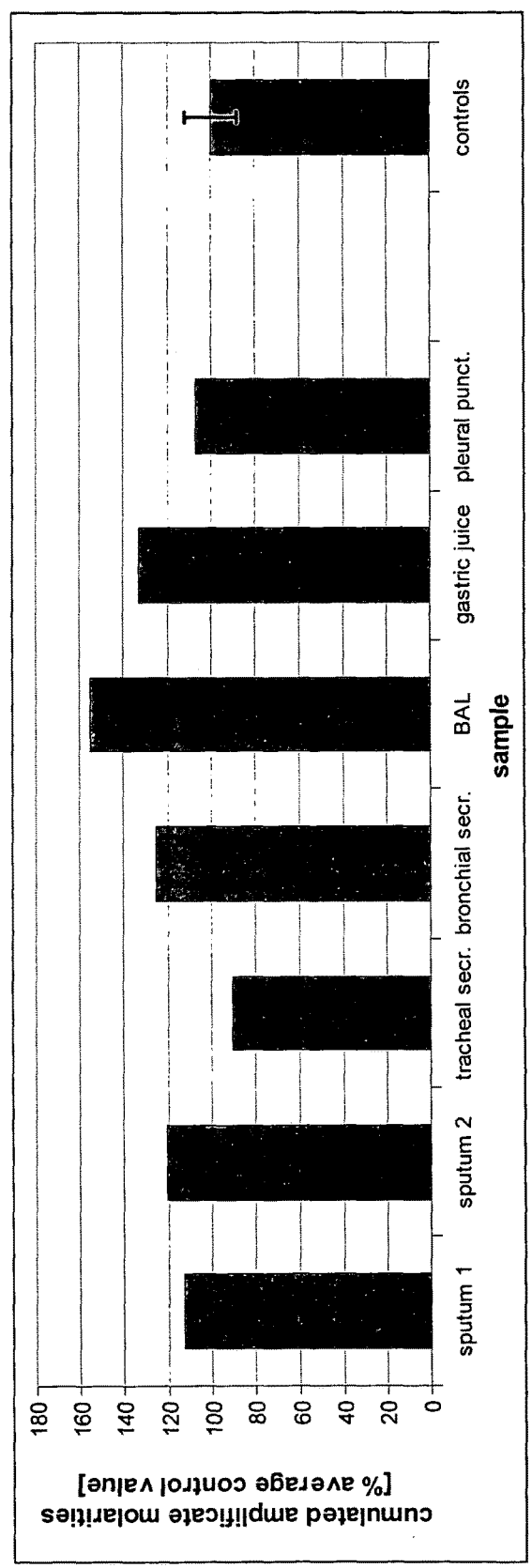

FIG. 9: PCR inhibition test of selected samples.

Putative co-purification of PCR inhibitors was tested by a PCR inhibition test for the eluates described in FIG. 8. For inhibition tests, 3 µl of a DNA eluate is added to a 30 µl PCR which contains an unrelated template with a corresponding primer mix. In absence of any inhibitory effect these primers generate several amplicons of known molarities. A significant decrease of amplicon molarities would indicate inhibition. For controls, eluates generated from phosphate buffered saline (PBS) were used. For evaluating the PCR efficiency and determining the presence of PCR inhibitors, the molarities of the amplicons generated in presence of the DNA isolated from the lysates of the present invention have been compared to the molarities of the amplicons generated by the control PCRs (control: n=4).

Figure 10:
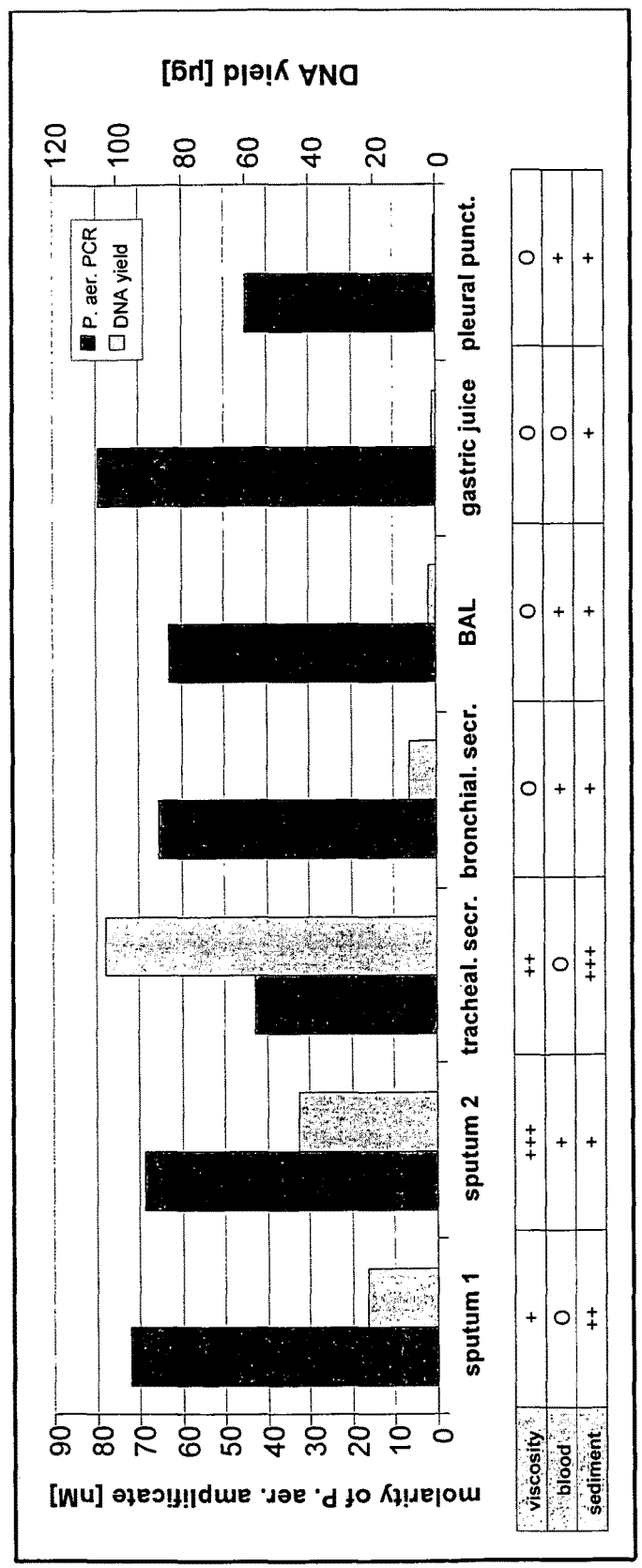

FIG. 10: PCR efficiency of isolated DNA (*P. aeruginosa* PCR).

PCRs specific for *P. aeruginosa* have been performed using DNA isolated from lysates of different bodily samples as described in FIG. 8. FIG. 10 shows the amplicon molarities and DNA yields of the different PCRs.

FIG. 11: PCR results of patient samples processed according to the method of the present invention.

27 patient samples have been processed using the manual lysis protocol as described in FIG. 1 and Example 1 (full lysis protocol). Silica membrane purified DNA was analyzed with multiplex PCRs detecting pathogens indicative for respiratory diseases (*Klebsiella pneumoniae, Streptococcus pneumoniae, Haemophilus influenzae, Staphylococcus aureus, Escherichia coli, Pseudomonas aeruginosa*, and *Streptococcus* species as indicator of host flora). Amplicon molarities have been determined using an Agilent Bioanalyzer.

Figure 12:

FIG. 12: Comparison of the PCR results with microbiological culture test data.

The PCR results shown in FIG. 11 have been compared to data derived from microbiological culture tests performed for the same samples as shown in FIG. 11. For five samples a pathogen genus has been identified by microbiological culture, however, for most of the samples microbiological culture did not result in the identification of the pathogens on a genus level. The results obtained by the microbiological culture tests have been confirmed by the PCR test. The *Haemophilus* primers used in this test do not discriminate between the species *influenzae* and *parainfluenzae*. In general, PCR allowed for detection and identification of pathogens in more samples than microbiological culture tests.

Figure 13:
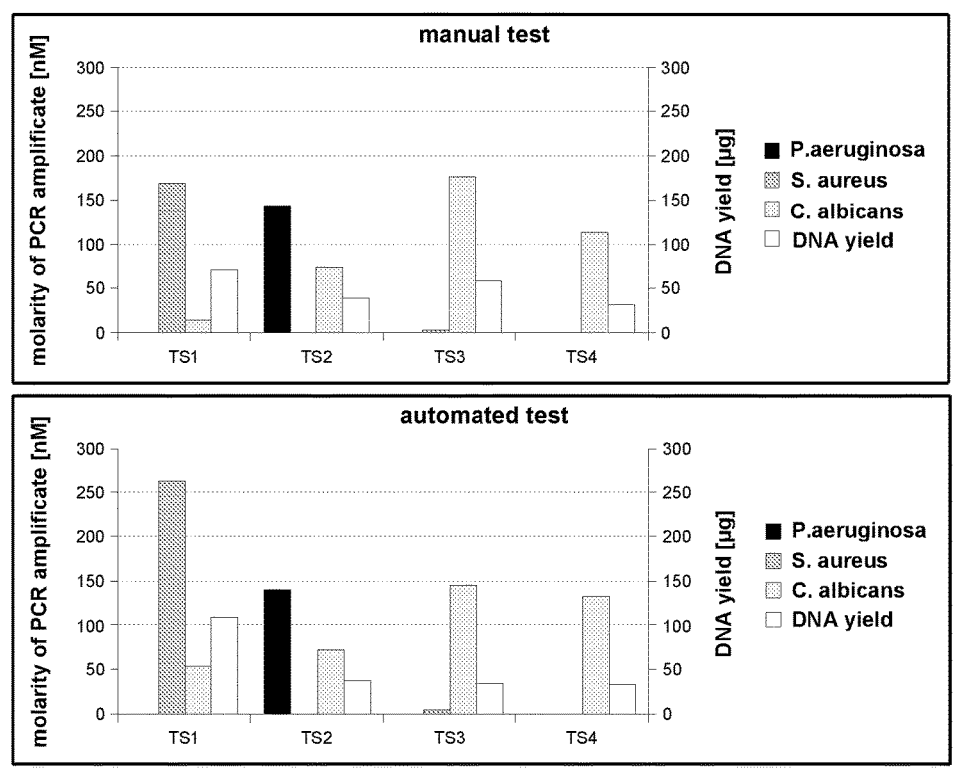

FIG. 13: Comparison of manual and automated lysis using clinical samples.

A device for full automation of the lysis process has been developed and performance was tested according to "process example B" (FIG. 2 and Example 1, full lysis protocol, automated process) and compared to the manual lysis protocol (FIG. 1 and Example 1, full lysis protocol, manual process) using clinical samples which have been tested positive by microbiological culture tests as indicated in the bottom panel. Tracheal secretions with high viscosities have been selected for this test. DNA isolated from the lysates using silica membranes, has been applied to triplex PCR using *Pseudomonas*-, *Staphylococcus*-, and *Candida*-specific primers.

Figure 14:
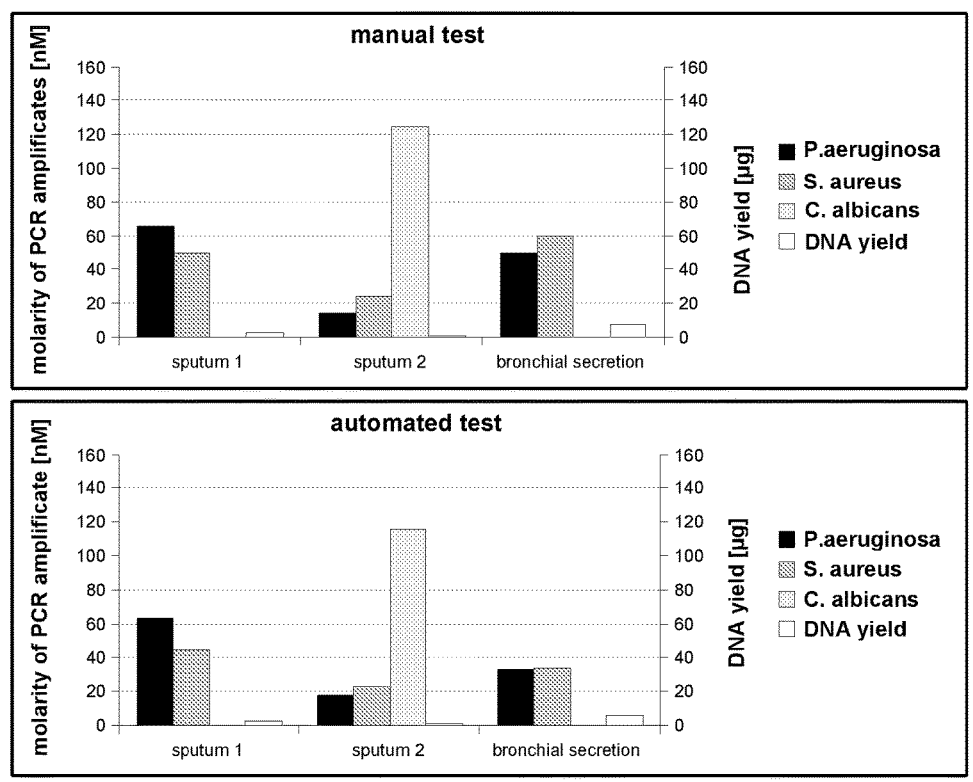

FIG. 14: Comparison of manual and automated lysis using spiked clinical samples.

To exclude any effects of sample freezing and thawing on pathogen lysis, a second set of samples was spiked with *Pseudomonas aeruginosa* (gram-negative) and *Staphylococcus aureus* (gram-positive) at 20000 pathogens/ml and processed with the manual or the automated protocol. DNA isolation and PCR has been performed as described for FIG. 13.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in a preferred embodiment the chaotropic agent of the lysis buffer of the invention is guanidinium hydrochloride and in another preferred embodiment the reducing agent of the lysis buffer is dithiothreitol, it is a preferred embodiment of the present invention that guanidinium hydrochloride and dithiothreitol are present in the lysis buffer according to the present invention.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, and recombinant DNA techniques which are explained in the literature in the field (cf., e.g., *Molecular Cloning: A Laboratory Manual*, 2$^{nd}$ Edition, J. Sambrook et al. eds., Cold Spring Harbor Laboratory Press, Cold Spring Harbor 1989).

Throughout this specification and the claims which follow, unless the context requires otherwise, the word "comprise" and variations, such as "comprises" and "comprising", will be understood to imply the inclusion of a stated member, integer, or step or group of members, integers, or steps, but not the exclusion of any other member, integer, or step or group of members, integers, or steps. The term "comprise" also encompasses the terms "essentially consisting of" and "consisting of" unless the context clearly dictates otherwise. As used in this specification and the appended claims, the singular forms "a", "an", and "the" include plural referents, unless the context clearly dictates otherwise.

Definitions

A "lysis buffer" in the context of the present invention is suitable for lysis of cells with the purpose of analyzing the contents of the cells, such as analyzing the nucleic acids contained in the cells. Preferably, the lysis buffer according to the present invention is suitable for the lysis of mammalian cells and/or microbial cells, such as bacterial and yeast cells. Thus, the lysis buffer of the present invention is preferably suitable for the lysis of bacteria of a family selected from the group consisting of Mycobacteriaceae, Pseudomonadaceae, Mycoplasmataceae, Chlamydiaceae, Enterobacteriaceae, Staphylococcaceae, Streptococcaceae, Xantomonadaceae, Moraxellaceae, Legionellaceae, Burkholderiaceae, Corynebacteriaceae, Neisseriaceae, Bacteroides, and Pasteurellaceae, and for the lysis of yeasts of a family selected from the group consisting of Saccharomycetaceae, Sporidiobolaceae, Trichocomaceae, and Pneumocystidaceae. The lytic properties of the lysis buffer according to the present invention may require processing steps such as heating of the sample to be lysed in said lysis buffer or bead milling. The processing steps may depend on the type of cells to be lysed and the type of sample the cells are contained in. Preferably, the lysis buffer according to the present invention is an aqueous lysis buffer, i.e., a lysis buffer based on water. Thus, a lysis buffer which, for example, consists of (i) at least one chaotropic agent, (ii) at least one reducing agent, and (iii) at least one proteolytic enzyme means in the context of the present invention that such lysis buffer may also contain water and optionally buffer components, e.g., for adjusting the pH of the lysis buffer.

The term "chaotropic agent" refers to an agent which disrupts the three dimensional structure of macromolecules such as proteins, DNA, or RNA and denatures them. Chaotropic agents interfere with stabilizing intra-molecular interactions mediated by non-covalent forces such as hydrogen bonds, van der Waals forces, and hydrophobic effects. Chaotropic ions are, for example, guanidinium, barium, thiocyanate, iodide, and perchlorate, according to the so called Hofmeister series (cations: $NH_4^+>Rb^+>K^+>Na^+>Cs^+>Li^+>Mg^{2+}>Ca^{2+}>Ba^{2+}>$guanidinium; anions: $PO_4^{3-}>SO_4^{2-}>HPO_4^{2-}>$acetate$>$citrate$>$tartrate$>Cl^->Br^->NO_3^->ClO_3^->ClO_4^->I^->SCN^-$). In the Hofmeister series, cations and anions on the left are said to be "kosmotropic" (or antichaotrope) and increase the strength of hydrophobic interactions. Ions on the right are "chaotropic" and tend to weaken hydrophobic interactions. For all aspects of the invention, the chaotropic agent contains at least one cation of the Hofmeister series which is further to the right in the series than calcium or at least one anion of the Hofmeister series which is further to the right in the series than the chlorate ($ClO_3^-$) anion. For example, the chaotropic agent in the context of the present invention may contain one of the following: barium, guanidinium, perchlorate, iodide, thiocyanate, or isothiocyanate. For example, the chaotropic agent in the context of all aspects of the present invention may be guanidinium thiocyanate, guanidinium isothiocyanate, guanidinium hydrochloride, guanidinium chloride, alkali thiocyanate, alkali isothiocyanate, alkali iodide, or alkali perchlorate. In this context, the alkali ion is preferably potassium or sodium.

A "reducing agent" in the context of the present invention is any agent that is capable of breaking up a disulfide bond in or within macromolecules such as proteins. For all aspects of the present invention the reducing agent may be dithiothreitol (DTT), N-acetyl-cysteine (NALC), beta-mercaptoethanol, Tris(2-Carboxyethyl) phosphine (TCEP), or thioredoxin. Preferably, the reducing agent is DTT.

The term "proteolytic enzyme" in the context of the present invention refers to any entity that possesses proteolytic activity, i.e., that is capable of catalyzing the hydrolysis of a protein, preferably the hydrolysis of a peptide bond. Preferably, the term "proteolytic enzyme" refers to an enzyme belonging to the group of enzymes with the Enzyme Commission number (EC number) EC 3.4, preferably EC 3.4.21 or EC 3.4.22. Preferably, the proteolytic enzyme is a protease, preferably a serine protease or a cysteine protease. The terms "protease", "peptidase", and "proteinase" are used interchangeably. Preferably, the proteolytic enzyme used in the present invention possesses broad substrate specificity. Preferably, the proteolytic enzyme is active in presence of one or more chaotropic agents. For example, it is preferred that the proteolytic enzyme used in the present invention is active in presence of 400 mM, preferably, 600 mM, preferably 800 mM, preferably 1 M guanidinium thiocyanate, and/or in presence of 2 M, preferably 3 M, preferably 4 M, preferably 5 M urea, and/or in presence of 1.5 M, preferably 2 M, preferably 4 M, preferably 5 M guanidinium hydrochloride. Preferably, the proteolytic enzyme used in the present invention is active in presence of one or more reducing agent. Thus, it is preferred that the proteolytic enzyme is active in presence of 10 mM DTT, preferably 20 mM, preferably 50 mM DTT, preferably 80 mM DTT, more preferably 100 mM DTT. In a particular preferred embodiment, the proteolytic enzyme is active in presence of about 20 mM DTT. In the context of the present invention, an enzyme such as a proteolytic enzyme, e.g., a protease, is considered active if the reaction rate of the reaction that is catalyzed by the enzyme is at least 10%, preferably at least 20%, preferably at least 30%, preferably at least 40%, preferably at least 50%, more preferably at least 60%, more preferably at least 70%, and even more preferably at least 80% of the maximal reaction rate of said enzyme using optimal conditions such as buffer and temperature conditions. Particularly preferred examples of proteolytic enzymes used in the present invention are proteinase K (preferably EC 3.4.21.64), subtilisin (preferably EC 3.4.21.62), elastase (preferably EC 3.4.21.11, EC 3.4.21.36, EC 3.4.21.37, or EC 3.4.21.71), caspase (preferably EC 3.4.22.36). In a particular preferred embodiment, the proteolytic enzyme is proteinase K, such as proteinase K obtainable from Qiagen (e.g., 20 mg/ml, >600 mAU/ml, ordering number 19131) or subtilisin. A preferred unit definition of proteinase K in the context of the present invention is: 1 unit is the activity that is necessary to release folin-positive amino acids and peptides corresponding to 1 µmole of tyrosine per minute. Another preferred unit definition of proteinase K in the context of the present invention is: 1 unit will hydrolyze urea-denatured hemoglobin to produce color equivalent to 1 µmole of tyrosine per minute at pH 7.5 at 37° C. The units "unit" and "mAU" (AU=Anson unit) are used interchangeably herein. The skilled person is well aware of how to choose different proteolytic enzymes to obtain a similar activity.

In the context of the present invention, the term "beads" refers to particles, which are preferably of a size in the range of 200 µm to 2 mm, preferably 300 µm to 800 µm. The beads may exhibit any shape, for example, they may be ball-shaped, cube-shaped, triangular-shaped, or they may exhibit any irregular shape. Preferably, the beads are made of a solid inert material. Thus, the beads preferably exhibit a firm consistency and preferably do not react chemically with biological substances such as proteins or nucleic acids to a significant extent. In particularly preferred embodiments, the beads do not bind nucleic acids to a significant extent. Preferably, the beads are made of glass, ceramics, plastics, or metal such as steel. The material of the beads is most preferably glass. Preferably, the term "beads" as used in the present invention does not refer to silica beads or any beads used for nucleic acid isolation.

The term "lysis" or "lysis reaction" refers to a lysis procedure and preferably relates to the lysis of a bodily sample as described herein. In the context of all aspects of the present invention, a lysis reaction preferably encompasses the provision of a lysis reaction mixture. A "lysis reaction mixture" in the context of the present invention preferably comprises a sample, preferably a bodily sample, at least one chaotropic agent, at least one reducing agent, and at least one proteolytic enzyme. Preferably, the lysis reaction mixture further comprises beads as described herein. For example, the lysis reaction mixture may be a mixture of the lysis buffer according to the first aspect of the present invention and a bodily sample or the lysis reaction mixture may be a mixture of the "pre-mixed lysis composition" as described herein, a bodily sample, and at least one proteolytic enzyme. Preferably, the nature and concentration of the at least one chaotropic agent and the at least one reducing agent are chosen such that the at least one proteolytic enzyme is active in the lysis reaction mixture. Preferably, the nature and concentration of the chaotropic agent and/or the nature and concentration of the reducing agent and/or the nature and concentration of the proteolytic enzyme is such that liquefaction, preferably lysis, of the bodily sample in the lysis reaction mixture is achieved. Preferably, the at least one chaotropic agent is as described herein, e.g., in the definitions and the first aspect of the present invention, and is preferably present in the lysis reaction mixture in a concentration in the range of 0.1 M to 4 M, preferably in the range of 0.5 M to 3.5 M, more preferably in the range of 1.0 M to 3.0 M, most preferably in the range of 1.2 M to 2.6 M. For example, the at least one chaotropic agent, preferably guanidinium hydrochloride, may be present in the lysis reaction mixture in a concentration of 0.5, 0.75, 1.0, 1.25, 1.5, 1.75, 2.0, 2.25, 2.5, 2.75, 3.0, 3.25, 3.5, 3.75, or 4.0 M, most preferably in a concentration of about 2.0±0.75 M. The skilled person will recognize that the optimal concentration of the chaotropic agent may vary for varying chaotropic agents, for example, depending on the sample type and/or the proteolytic enzyme. For example, the preferred concentration of guanidinium hydrochloride in the lysis reaction mixture is in the range of 1.0 to 3.0 M, preferably 2.0±0.75 M, while the preferred concentration for guanidinium thiocyanate is in the range of 0.1 to 1.0 M, preferably 0.5±0.4 M, for example, 0.1, 0.2, 0.3, 0.4, 0.5, 0.6, 0.7, 0.8, or 0.9 M. In some embodiments, the at least one chaotropic agent in the sense of the present invention is a commercially available lysis buffer which contains as a component a chaotropic agent, preferably as a main component, for example, the Qiagen lysis buffer AL, as described for the first aspect of the present invention. In these embodiments, the lysis reaction mixture preferably comprises the commercially available lysis buffer, preferably the Qiagen lysis buffer AL, in a concentration in the range of 20% (vol/vol) to 80% (vol/vol), preferably in the range of 30% (vol/vol) to 70% (vol/vol), more preferably in the range of 40% (vol/vol) to 60% (vol/vol). For example, the commercially available lysis buffer, preferably the Qiagen lysis buffer AL, may be present in the lysis reaction mixture in a concentration of 20% (vol/vol), 30% (vol/vol), 40% (vol/vol), 50% (vol/vol), 60% (vol/vol), 70% (vol/vol), or 80% (vol/vol), preferably in a concentration of 50±10% (vol/vol), more preferably 50±5% (vol/vol). The skilled person will understand that the vol % of commercially available lysis buffer present in the lysis reaction mixture is dependent on the type and/or the concentration of the chaotropic agent in said commercially available lysis buffer and will be readily able to adapt the vol % of commercially available lysis buffer in the lysis reaction mixture based on the type and/or the concentration of the chaotropic agent in the commercially available lysis buffer. Preferably, the at least one reducing agent is as described herein and is preferably present in the lysis reaction mixture in a concentration in the range of 0.5 mM to 100 mM, preferably in the range of 2.5 mM to 50 mM, more preferably in the range of 10 mM to 30 mM. For example, the at least one reducing agent, preferably DTT, may be present in the lysis reaction mixture in a concentration of 0.5 mM, 1.0 mM, 5.0 mM, 10 mM, 15 mM, 20 mM, 25 mM, 30 mM, 40 mM, 50 mM, 60 mM, 70 mM, 80 mM, 90 mM, or 100 mM, preferably the concentration is above 10 mM, preferably about 20±5 mM, more preferably about 20 mM. Preferably, the at least one proteolytic enzyme is as described herein and is preferably present in the lysis reaction mixture in a concentration in the range of 5 to 200 units/ml, preferably between 10 to 100 units/ml, more preferably between 20 to 50 units/ml. For example, the proteolytic enzyme, preferably proteinase K, may be present in the lysis reaction mixture in a concentration of about 5, 10, 15, 20, 25, 30, 35, 40, 45, 50, 55, 60, 65, 70, 75, 80, 85, 90, 95, or 100 units/ml, preferably in a concentration of 25±10 units/ml, most preferably in a concentration of 25±5 units/ml, wherein preferably the unit definitions are as described above for proteinase K. Preferably, the optional beads are as described herein and are preferably present in the lysis reaction mixture in a concentration in the range of 50 to 500 mg/ml, preferably in the range of 100 to 400 mg/ml, more preferably in the range of 150 to 350 mg/ml, most preferably in the range of 250 to 350 mg/ml. For example, the optional beads may be present in the lysis reaction mixture in a concentration of 50, 100, 150, 200, 250, 300, 350, 400, 450, or 500 mg/ml, preferably in a concentration of 300±100 mg/ml, more preferably in a concentration of 300±50 mg/ml. It is to be understood that the concentrations and percentages (e.g., vol %) provided herein do not consider the volume of the optional beads. In some embodiments, the lysis reaction mixture does not contain detergents and/or chelating agents as described herein, e.g., in the definitions and for the lysis buffer according to the first aspect of the present invention. In some embodiments, the lysis reaction mixture further comprises one or more detergents and/or one or more chelating agents as described herein. Preferably, the lysis reaction mixture is based on water and preferably contains buffering components, such as those described for the lysis buffer according to the first aspect of the present invention. Preferably, the pH of the lysis reaction mixture is approximately neutral to alkaline. Preferably, the pH of the lysis reaction mixture is in the range of 5.5 to 8.0, i.e., 5.5, 6.0, 6.5, 7.0, 7.5, or 8.0, preferably around 7. Preferably, the lysis reaction mixture does not contain any other enzymes than the at least one proteolytic enzyme. For example, the lysis reaction mixture may comprise, preferably essentially consist of, preferably consist of a bodily sample as described herein, 1.2 to 2.6 M chaotropic agent, preferably guanidinium hydrochloride, 21±5 mM reducing agent, preferably DTT, 25±5 units proteolytic enzyme, preferably proteinase K, and preferably 300±50 mg/ml beads. For example, the lysis reaction mixture may consist of about 48±3% (vol/vol) Qiagen lysis buffer AL, e.g., 230 µl±10 µl, about 2% (vol/vol) 1 M DTT, e.g., 10 µl±3 µl, about 4% (vol/vol) (>600 mAU/ml) proteinase K, e.g., 20 µl±6 µl, about 46±5% (vol/vol) bodily sample, and preferably about 300 mg/ml±50 mg/ml beads, e.g., 140±30 mg glass beads. Proteinase K may also be added to the lysis reaction mixture in dried form.

The term "pre-mixed lysis composition" refers to a composition comprising at least one chaotropic agent and at least one reducing agent. Preferably, the pre-mixed lysis composition further comprises beads as described herein. Preferably, the pre-mixed lysis composition is the lysis buffer according to the first aspect of the present invention lacking the at least one proteolytic enzyme. Preferably, the nature and concentration of the chaotropic agent and/or the nature and concentration of the reducing agent in the pre-mixed lysis composition is such that liquefaction, preferably lysis, of a bodily sample is achieved if said bodily sample is mixed with the pre-mixed lysis composition, preferably if said bodily sample is mixed with the pre-mixed lysis composition in a volume ratio of about 1:1. Preferably, the nature and concentration of the chaotropic agent and/or the nature and concentration of the reducing agent in the pre-mixed lysis composition is such that a proteolytic enzyme is active in a mixture of the pre-mixed lysis composition and a bodily sample, preferably if the pre-mixed lysis composition is mixed with a bodily sample in a volume ratio of about 1:1. Preferably, the concentration of the at least one chaotropic agent and the at least one reducing agent in the pre-mixed lysis composition is such that after mixing it with a bodily sample and addition of a proteolytic enzyme, the concentrations of the at least one chaotropic agent and the at least one reducing agent is as defined for the lysis reaction mixture. Preferably, the at least one chaotropic agent is as described herein, e.g., in the definitions and the first aspect of the present invention, and is preferably present in the pre-mixed lysis composition in a concentration in the range of 0.2 M to 8.0 M, preferably in the range of 1.0 M to 7.0 M, more preferably in the range of 2.0 M to 6.0 M, most preferably in the range of 2.5 M to 5.2 M. For example, the at least one chaotropic agent, preferably guanidinium hydrochloride, may be present in the pre-mixed lysis composition in a concentration of about 1.0, 1.5, 2.0, 2.5, 3.0, 3.5, 4.0, 4.5, 5.0, 5.5, 6.0, 6.5, 7.0, 7.5, or 8.0 M, most preferably in a concentration of about 4.0±1.5 M. The skilled person will recognize that the optimal concentration of the chaotropic agent may vary for varying chaotropic agents, for example, depending on the sample type and/or the proteolytic enzyme. For example, the preferred concentration of guanidinium hydrochloride in the pre-mixed lysis composition is in the range of 2.0 to 6.0 M, preferably 4.0±1.5 M, while the preferred concentration for guanidinium thiocyanate is in the range of 0.2 to 2.0 M, preferably 1.0±0.8 M, for example, 0.2, 0.3, 0.4, 0.5, 0.6, 0.7, 0.8, 0.9, 1.0, 1.1, 1.2, 1.3, 1.4, 1.5, 1.6, 1.7, or 1.8 M. In some embodiments, the at least one chaotropic agent in the sense of the present invention is a commercially available lysis buffer which contains as a component a chaotropic agent, preferably as a main component, for example, the Qiagen lysis buffer AL, as described for the first aspect of the present invention. In these embodiments, the pre-mixed lysis composition preferably comprises the commercially available lysis buffer, preferably the Qiagen lysis buffer AL, in a concentration in the range of 40% (vol/vol) to 99% (vol/vol), preferably in the range of 60% (vol/vol) to 98% (vol/vol), more preferably in the range of 80% (vol/vol) to 96% (vol/vol). For example, the commercially available lysis buffer, preferably the Qiagen lysis buffer AL, may be present in the pre-mixed lysis composition in a concentration of 50% (vol/vol), 60% (vol/vol), 70% (vol/vol), 80% (vol/vol), 90% (vol/vol), 95% (vol/vol), or 98% (vol/vol), preferably in a concentration of 90±9% (vol/vol), more preferably 96±3% (vol/vol). The skilled person will understand that the vol % of commercially available lysis buffer present in the pre-mixed lysis composition is dependent on the type and/or the concentration of chaotropic agent in said commercially available lysis buffer and will be readily able to adapt the vol % of commercially available lysis buffer in the pre-mixed lysis composition based on the type and/or the concentration of the chaotropic agent in the commercially available lysis buffer. Preferably, the at least one reducing agent is as described herein, e.g., in the definitions and the first aspect of the present invention, and is preferably present in the pre-mixed lysis composition in a concentration in the range of 1.0 mM to 200 mM, preferably in the range of 5.0 mM to 100 mM, more preferably in the range of 20 mM to 60 mM. For example, the at least one reducing agent, preferably DTT, may be present in the pre-mixed lysis composition in a concentration of 1.0 mM, 5.0 mM, 10 mM, 20 mM, 30 mM, 40 mM, 50 mM, 60 mM, 70 mM, 80 mM, 90 mM, 110 mM, 120 mM, 130 mM, 140 mM, 150 mM, 160 mM, 170 mM, 180 mM, 190 mM, or 200 mM, preferably the concentration is above 20 mM, preferably the concentration is about 40±10 mM, more preferably about 40 mM. Preferably, the optional beads are as described herein and are preferably present in the pre-mixed lysis composition in a concentration in the range of 100 to 1000 mg/ml, preferably in the range of 200 to 800 mg/ml, more preferably in the range of 300 to 700 mg/ml, most preferably in the range of 500 to 700 mg/ml. For example, the optional beads may be present in the pre-mixed lysis composition in a concentration of 100, 200, 300, 400, 500, 600, 700, 800, 900, or 1000 mg/ml, preferably in a concentration of 600±200 mg/ml, more preferably in a concentration of 600±100 mg/ml. It is to be understood that the concentrations provided herein are calculated without the volume of the optional beads. In some embodiments, the pre-mixed lysis composition does not contain detergents and/or chelating agents as described herein, e.g., in the definitions or for the lysis buffer according to the first aspect of the present invention. In some embodiments, the pre-mixed lysis composition further comprises one or more detergents and/or one or more chelating agents as described herein. Preferably, the pre-mixed lysis composition is based on water and preferably contains buffering components, such as those described for the lysis buffer according to the first aspect of the present invention. Preferably, the pH of the pre-mixed lysis composition is approximately neutral to alkaline. Preferably, the pH of the pre-mixed lysis composition is in the range of 5.5 to 8.0, i.e., 5.5, 6.0, 6.5, 7.0, 7.5, or 8.0, preferably around 7. Preferably, the pre-mixed lysis composition does not contain a proteolytic enzyme, preferably the pre-mixed lysis composition does not contain any enzyme. For example, the pre-mixed lysis composition may comprise, preferably essentially consist of, preferably consist of a chaotropic agent, preferably guanidinium hydrochloride, in a concentration in the range of 2 to 6 M, preferably, 2.5 to 5.5 M, more preferably 2.5 to 5.1 M, a reducing agent, preferably DTT, in a concentration in the range of 20 to 60 mM, preferably 40±10 mM, and preferably beads, preferably in a concentration in the range of 600±100 mg/ml. For example, the pre-mixed lysis composition may comprise, preferably essentially consist of, preferably consist of 96±3% (vol/vol) Qiagen lysis buffer AL, e.g., 230 µl±10 µl, 4±1% (vol/vol) 1 M DTT, e.g., 10±3 µl, and preferably beads, preferably in a concentration of 600±100 mg/ml, e.g., 140±30 mg glass beads.

In the context of the lysis buffer according to the present invention, the pre-mixed lysis composition, and the lysis reaction mixture, in some embodiments, the chaotropic agent is not guanidinium thiocyanate if the reducing agent is DTT. In some embodiments, the reducing agent is not DTT if the chaotropic agent is guanidinium thiocyanate or urea. In some embodiments, the reducing agent is not DTT. In some embodiments, the reducing agent is not beta-mercaptoethanol. In some embodiment, the chaotropic agent is not guanidinium thiocyanate. In some embodiments, the chaotropic agent is not urea.

The terms "wherein the nature and concentration of the chaotropic agent is such that liquefaction, preferably lysis, of a bodily sample is achieved", "wherein the nature and concentration of the reducing agent is such that liquefaction, preferably lysis, of a bodily sample is achieved", and "wherein the nature and concentration of the proteolytic enzyme is such that liquefaction, preferably lysis, of a bodily sample is achieved" mean that the chaotropic agent and/or the reducing agent and/or the proteolytic enzyme and their concentrations are chosen based on their ability to liquefy, preferably lyse a bodily sample, preferably a viscous bodily sample. In particular, this means preferably that the bodily sample exhibits a higher viscosity before treatment with the chaotropic agent and/or the reducing agent and/or the proteolytic enzyme compared to the viscosity after said treatment. Preferably, the viscosity before treatment is at least 2-, 3-, 4-, 5-, 6-, 7-, 8-, 9-, or 10-fold higher than after treatment, most preferably the viscosity before treatment is 10-fold higher than after the treatment. Thus, in order to determine the nature of the chaotropic agent and/or the reducing agent and/or the proteolytic enzyme as well as the appropriate concentrations thereof, the skilled person may incubate a bodily sample, preferably a viscous bodily sample, such as sputum or tracheal secretion, with the candidate chaotropic agent and/or reducing agent and/or proteolytic enzyme at various concentrations, for example, at 0.2 M, 0.5 M, 1M, 2 M, 3 M, 4 M, 5 M, and 6 M for the chaotropic agent and/or at 1 mM, 5 mM, 10 mM, 25 mM, 50 mM, and 100 mM for the reducing agent and/or at 5, 10, 15, 20, 25, 30, 35, 40, 45, 50, 55, 60, 65, 70, 75, 80, 85, 90, 95, or 100 units/ml for the proteolytic enzyme, for a certain period of time, such as for 5 minutes, 10 minutes, 20 minutes, or 30 minutes, in case of the proteolytic enzyme preferably at a temperature at which the proteolytic enzyme is active, and determine the viscosity of the sample before and after the treatment. Regarding the lysis properties, the above expressions mean that the bodily sample contains a higher number of intact cells before treatment with the chaotropic agent and/or the reducing agent and/or the proteolytic enzyme compared to the number of cells after said treatment. Preferably, the number of intact cells before treatment is at least 2-, 3-, 4-, 5-, 6-, 7-, 8-, 9-, or 10-fold higher than after treatment, most preferably the number of intact cells before treatment is 10-fold higher than after the treatment. Thus, in order to determine the nature of the chaotropic agent and/or the reducing agent and/or the proteolytic enzyme as well as the appropriate concentrations thereof, the skilled person may incubate a bodily sample, as described above and the number of intact cells in the sample is determined before and after treatment, for example, by microscopic analyses. Then the chaotropic agent and/or the reducing agent and/or the proteolytic enzyme are chosen in concentrations suitable to liquefy, preferably lyse the bodily sample as specified above.

The term "bodily sample" as used in the present invention refers to any sample that is derived from the body of an individual. In this context, the term "individual" preferably refers to an animal, preferably a mammalian animal including a human being. For example, an individual in the context of the present invention may be a mouse, rat, guinea-pig, rabbit, cat, dog, goat, sheep, pig, cow, horse, or human, preferably a human. The individual may be a patient, wherein the term "patient" refers to an individual suffering from a disease or being suspected of suffering from a disease. In the context of the present invention, the disease is preferably a respiratory disease. Preferably, a bodily sample is a bodily fluid or bodily tissue, preferably taken for the purpose of a scientific test, such as for diagnosing a disease, e.g., a respiratory disease, for example, by detecting and/or identifying a pathogen or the presence of a tumor marker in a bodily sample which is preferably relevant for the diagnosis of a respiratory disease. Preferably, a bodily sample in the context of the present invention comprises cells, for example, pathogens or cells of the individual the bodily sample originated from, for example, tumor cells.

In the context of the present invention, the preferred bodily samples are samples that are relevant for the diagnosis of a respiratory disease. Such bodily samples may be respiratory samples, i.e., bodily samples derived from the respiratory tract, and non-respiratory samples, i.e., bodily samples that are not derived from the respiratory tract. The respiratory tract in the context of the present invention preferably comprises the nose, nasal passages, paranasal sinuses, throat, pharynx, voice box, larynx, trachea, bronchi, bronchioles, and lungs, including respiratory bronchioles, alveolar ducts, alveolar sacs, and alveoli. Examples for respiratory samples in the context of the present invention are sputum, pus (e.g., pus from the paranasal cavity), bronchial secretion, tracheal secretion, endotracheal secretion, bronchial aspirates, tracheal aspirates, endotracheal aspirates, bronchial lavage, bronchoalveolar lavage (BAL), bronchial swab, nasopharyngeal swab, laryngeal swab, and lung biopsies. Preferred non-respiratory samples used in the present invention are relevant for the diagnosis of respiratory diseases. Preferred examples of non-respiratory samples in the context of the present invention are blood, pus, pleural fluid, pleural punctates, gastric juice, gastric aspirates, and drainages or punctate fluids from other body locations.

The expression "different types of bodily samples" refers to two or more bodily samples which are different in nature. For example, the different types of bodily samples may differ in their consistency, e.g., liquid, viscous, chunky, solid etc., and/or their composition, e.g., structure and nature of the components (proteins, lipids, mucins, cells, extracellular matrix, tissue, membranes, salts, polysaccharides, water, etc.) pH etc, or their origin. The degree of difference between samples may be different for different sample types. Thus, the more features of two samples are different, the more differing are the samples. For example, blood and sputum or gastric juice and sputum are highly different, while sputum and tracheal secretion are less different etc.

The term "universally applicable" as used in the present invention means "broadly usable". A universally applicable lysis buffer is thus a broadly usable lysis buffer. For example, a lysis buffer which is universally applicable for the lysis of samples, such as bodily samples, is preferably applicable for the lysis of several different types of samples, for example, of at least 2, preferably at least 3, preferably at least 4, preferably at least 5, more preferably at least 6, more preferably at least 7, more preferably at least 8, even more preferably at least 9, and most preferably at least 10 different types of bodily samples. Preferably, the universally applicable lysis buffer is effective in lysing several different types of samples. Most preferably, a lysis buffer which is universally applicable is applicable for the lysis of several, preferably at least 2, highly different types of bodily samples as described below. Preferably, the term "applicable to" in the context of the present invention means "effective in" or "suitable for".

In the context of the present invention, the expressions "effective in lysing several different types of samples" and "suitable for the lysis of two or more different types of bodily samples" preferably mean that at least 10%, preferably at least 20%, preferably at least 30%, preferably at least 40%, more preferably at least 50%, more preferably at least 60%, more preferably at least 70%, even more preferably at least 80%, even more preferably at least 90%, even more preferably at least 95%, most preferably at least 99% of the cells contained in the bodily sample are lysed in at least 2, preferably at least 3, preferably at least 4, preferably at least 5, more preferably at least 6, more preferably at least 7, more preferably at least 8, even more preferably at least 9, and most preferably at least 10 different types of bodily samples.

In the context of the present invention "a broad spectrum of bodily samples" means at least 2, preferably at least 3, preferably at least 4, preferably at least 5, more preferably at least 6, more preferably at least 7, more preferably at least 8, even more preferably at least 9, and most preferably at least 10 different types of bodily samples. In a preferred embodiment, "a broad spectrum of bodily samples" refers to "a broad spectrum of bodily samples relevant for the diagnosis of a respiratory disease". Most preferably, "a broad spectrum of bodily samples" refers to several, preferably at least 2, highly different types of bodily samples as described below. A "universally applicable lysis buffer" in the context of the present invention is preferably applicable for the lysis of a "broad spectrum of bodily samples". In this context, a universally applicable lysis buffer is a broad-spectrum lysis buffer.

Preferably, the lysis buffer, the use, the methods, and/or the kit according to the present invention is/are universally applicable, preferably to the lysis of bodily samples, preferably to the lysis of bodily samples relevant for the diagnosis of a respiratory disease, and/or are applicable to the lysis of a broad spectrum of bodily samples. This means, for example, that the lysis buffer, the use, the methods, or the kit according to the present invention is/are applicable, preferably applied to the lysis of at least 2, preferably at least 3, preferably at least 4, preferably at least 5, more preferably at least 6, more preferably at least 7, more preferably at least 8, even more preferably at least 9, and most preferably at least 10 different types of bodily samples selected from the group consisting of blood, sputum, pus (e.g., pus from the paranasal cavity), pleural fluid, pleural punctates, bronchial secretion, tracheal secretion, endotracheal secretion, bronchial aspirates, tracheal aspirates, endotracheal aspirates, bronchial lavage, bronchoalveolar lavage (BAL), bronchial swab, nasopharyngeal swab, laryngeal swab, gastric juice, gastric aspirates, and lung biopsies, or that the lysis buffer, the use, the methods, or the kit according to the present invention is/are applicable, preferably applied to the lysis of at least 2, preferably at least 3, more preferably at least 4, more preferably at least 5, most preferably at least 6 types of bodily samples selected from the group consisting of blood, sputum, tracheal secretion, bronchial secretion, bronchoalveolar lavage, gastric juice, and pleural punctate, or that the lysis buffer, the use, the methods, or the kit according to the present invention is/are applicable, preferably applied to the lysis of at least 2, preferably at least 3 types of bodily samples selected from the group consisting of blood, secretions (such as tracheal secretions, bronchial secretions etc.), sputum, and lavages (such as bronchial lavages, bronchoalveolar lavages etc.), for example, blood and secretions; blood and sputum; blood and lavages; secretions and sputum; secretions and lavages; sputum and lavages; blood, secretions, and lavages; blood, secretions, and sputum, blood, sputum, and lavages; secretions, sputum, and lavages; and blood, secretions, sputum, and lavages.

In particularly preferred embodiments, the lysis buffer, the use, the methods, or the kit according to the present invention is/are applicable, preferably applied to the lysis of samples comprising, essentially consisting of, or consisting of blood, sputum, tracheal secretion, bronchial secretion, bronchoalveolar lavage, gastric juice, and pleural punctate.

Preferably, the lysis buffer, the use, the methods, or the kit according to the present invention is/are applicable, preferably applied to the lysis of at least 2 highly different types of bodily samples, such as blood and sputum; blood and tracheal secretion; blood and bronchial secretion; blood and bronchoalveolar lavage; blood and gastric juice; blood and pleural punctate; sputum and gastric juice; sputum and pleural punctate; bronchoalveolar lavage and pleural punctate; bronchoalveolar lavage and gastric juice; bronchoalveolar lavage and sputum; and pleural punctate and gastric juice. More preferably, the lysis buffer, the use, the methods, or the kit according to the present invention is/are applicable, preferably applied to the lysis of at least 3 highly different samples, such as blood, sputum, and gastric juice; blood, sputum, and pleural punctate; blood, tracheal secretion, and gastric juice; blood, tracheal secretion, and pleural punctate; blood, bronchial secretion, and gastric juice; blood, bronchial secretion, and pleural punctate; blood, bronchoalveolar lavage, and gastric juice; blood, bronchoalveolar lavage, and pleural punctate; sputum, gastric juice, and pleural punctate; tracheal secretion, gastric juice, and pleural punctate; bronchial secretion, gastric juice, and pleural punctate; and bronchoalveolar lavage, gastric juice, and pleural punctate.

A "respiratory disease" in the context of the present invention is any disease affecting the respiratory system. For example, respiratory diseases as used herein include (i) obstructive lung diseases, (ii) restrictive lung diseases, (iii) respiratory tract infections, such as upper respiratory tract infections, e.g., common cold, sinusitis, tonsillitis, otitis media, pharyngitis, or laryngitis, and lower respiratory tract infections, e.g., pneumonia, (iv) respiratory tumors, e.g., small cell lung cancer, non-small cell lung cancer (e.g., adenocarcinoma, large cell undifferentiated carcinoma), other lung cancers such as carcinoid, Kaposi's sarcoma, or melanoma, lymphoma, head and neck cancer, mesothelioma, and cancer metastasis in the lung such as from breast cancer, colon cancer, prostate cancer, germ cell cancer, and renal cell carcinoma, (v) pleural cavity diseases, e.g., empyema and mesothelioma, and (vi) pulmonary vascular diseases. Particular preferred respiratory diseases in the context of the present invention are respiratory diseases that can be diagnosed using molecular diagnostics, preferably using nucleic acid amplification and analysis methods. For example, respiratory tract infections, such as infections with pathogens, e.g., bacteria, viruses, yeast, or fungi, preferably yeast or bacteria, and respiratory tumors are preferred respiratory diseases in the context of the present invention. Particularly preferred respiratory diseases in the context of the present invention are pneumonias, in particular pneumonias caused by infections with pathogens, such as bacterial, viral, fungal, parasitic, atypical, community-acquired, healthcare-associated, hospital-acquired, ventilator-acquired pneumonia, or severe acute respiratory syndrome, tuberculosis, bronchitis, pathogenic infections during cystic fibrosis or chronic obstructive pulmonary disease (COPD), and a respiratory tumor.

The term "detergent" as used herein means "surfactant". Examples for detergents are alkyl sulfate salts, such as sodium dodecyl sulfate (SDS) or ammonium lauryl sulfate, non-ionic surfactants, such as Triton X-100, octyl glucoside, Genapol X-100, or polysorbates, e.g., Tween 20 or Tween 80, and sarkosyl (N-lauroyl-sarcosine). In some embodiments, the lysis buffer according to the present invention, the pre-mixed lysis composition, and/or the lysis reaction mixture do not contain a detergent. Preferably, the lysis buffer according to the present invention, the pre-mixed lysis composition, and/or the lysis reaction mixture do not contain SDS. Preferably, the lysis buffer according to the present invention, the pre-mixed lysis composition, and/or the lysis reaction mixture do not contain Triton X-100. Preferably, the lysis buffer according to the present invention, the pre-mixed lysis composition, and/or the lysis reaction mixture dos not contain Tween 20 or Tween 80. Preferably, the lysis buffer according to the present invention, the pre-mixed lysis composition, and/or the lysis reaction mixture do not contain N-lauroyl-sarcosine. Preferably, the lysis buffer according to the present invention, the pre-mixed lysis composition, and/or the lysis reaction mixture do not contain any of the above detergents, more preferably, the lysis buffer, the pre-mixed lysis composition, and/or the lysis reaction mixture do not contain any detergent. In some embodiments, the lysis buffer according to the present invention, the pre-mixed lysis composition, and/or the lysis reaction mixture contain one or more detergents, for example, one or more of the above detergents. For example, the lysis reaction mixture may contain one or more detergents in a concentration in the range of 0.1 to 10% (w/v), preferably 0.25 to 5% (w/v), such as 0.25, 0.5, 0.75, 1.0, 1.25, 1.5, 1.75, 2.0, 2.5, or 3% (w/v). For example, the lysis buffer according to the present invention or the pre-mixed lysis composition may contain one or more detergents in a concentration in the range of 0.2 to 20% (w/v), preferably 0.5 to 10% (w/v), such as 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10% (w/v). For example, if the lysis buffer according to the present invention, the pre-mixed lysis composition or the lysis reaction mixture comprises the Qiagen lysis buffer AL as chaotropic agent, the lysis buffer according to the present invention, the pre-mixed lysis composition or the lysis reaction mixture may contain a detergent if the Qiagen lysis buffer AL contains a detergent. In this case, the lysis buffer, the pre-mixed lysis composition, and/or the lysis reaction mixture may contain the specific detergent which is present in the Qiagen lysis buffer AL and/or any additional detergent. For example, the lysis buffer according to the present invention, the pre-mixed lysis composition, and/or the lysis reaction mixture may contain Triton X-100, Tween 20 and/or Tween 80, e.g., in a concentration as described above. Preferably, the nature and concentration of the one or more detergents is chosen such that the proteolytic enzyme used in the present invention is active.

The term "chelating agent" as used in the present invention refers to a "polydentate ligand". The terms "chelating agent", "chelator", "chelant", and "sequestering agent" are used interchangeably. Preferably, the chelating agent is capable of forming multiple bindings to a single atom such as a metal ion, e.g., $Mg^{2+}$ or $Ca^{2+}$. Examples for chelating agents are acetylacetone, ethylenediamine, diethylenetriamine, iminodiacetate, triethylenetetramine, triaminotriethylamine, nitrilotriacetate, ethylenediaminotriacetate, ethylenediaminetetraacetic acid (EDTA), ethylene glycol tetraacetic acid (EGTA), diethylene triamine pentaacetic acid (DTPA), and 1,4,7,10-tetraazacyclododecane-1,4,7,10-tetraacetic acid (DOTA). In some embodiments, the lysis buffer according to the present invention, the pre-mixed lysis composition, and/or the lysis reaction mixture do not contain EDTA and/or EGTA. More preferably, the lysis buffer according to the present invention, the pre-mixed lysis composition, and/or the lysis reaction mixture do not contain any of the above chelating agents, most preferably, the lysis buffer, the pre-mixed lysis composition, and/or the lysis reaction mixture do not contain any chelating agent. In some embodiments, the lysis buffer according to the present invention, the pre-mixed lysis composition, and/or the lysis reaction mixture contain one or more chelating agents, for example, one or more of the above chelating agents. For example, the lysis reaction mixture may contain one or more chelating agents in a concentration in the range of 0.5 to 100 mM, preferably 1 to 50 mM, such as in a concentration of about 1, 2, 5, 10, 15, 20, 25, 30, 35, 40, 45, or 50 mM. For example, the pre-mixed lysis composition or the lysis buffer according to the present invention may contain one or more chelating agents in a concentration in the range of 1 to 200 mM, preferably 5 to 100 mM, such as in a concentration of about 5, 10, 15, 20, 25, 30, 35, 40, 45, 50, 60, 70, 80, 90, or 100 mM. For example, if the lysis buffer according to the present invention, the pre-mixed lysis composition, or the lysis reaction mixture comprises the Qiagen lysis buffer AL as chaotropic agent, the lysis buffer according to the present invention, the pre-mixed lysis composition, or the lysis reaction mixture may contain a chelating agent if the Qiagen lysis buffer AL contains a chelating agent. In this case, the lysis buffer may contain the specific chelating agent which is present in the Qiagen lysis buffer AL or any additional chelating agent. For example, the lysis buffer according to the present invention, the pre-mixed lysis composition, or the lysis reaction mixture may contain EDTA or EGTA in a concentration as described above. Preferably, the concentration of the chelating agent is chosen such that the proteolytic enzyme used in the present invention is active.

The term "processing" in the context of the present invention refers in general to every treatment that comprises a change in one or more physical properties of a sample being processed when said physical property/properties is/are determined before and after the treatment/processing. Preferably, "processing" in the sense of the present invention comprises liquefaction of a sample such that the viscosity of the sample is reduced by the processing procedure. It is particularly preferred that "processing" comprises lysis of the sample, meaning the disintegration of cells present in the sample. Such cells may be prokaryotic or eukaryotic cells, for example, bacterial cells, yeast cells, fungal cells, animal cells, mammalian cells etc., wherein processing may lead to lysis of all cells in the sample or only of a specific type of cells or a subset of bacteria. In the context of the present invention, it is most preferred that processing comprises the lysis of a pathogen.

The term "liquefaction" in the context of the present invention means that the viscosity of a viscous sample before liquefaction is higher, preferably at least 2-fold higher compared to the viscosity after liquefaction. Preferably, the viscosity of the sample is at least 3-fold higher before liquefaction compared to the viscosity after liquefaction. More preferably, the viscosity of the sample is at least 5-fold, most preferably at least 10-fold higher before liquefaction compared to the viscosity after liquefaction.

"Viscosity" in the context of the present invention means dynamic viscosity, i.e., η, which is measured in $kg \cdot m^{-1} \cdot s^{-1} = Pa \cdot s$. Another common unit for dynamic viscosity is centipoise (cP), wherein 1 cP equals 1 mPa·s. Water at 20° C. has a viscosity of 1.0020 cP. Some examples for materials with higher viscosities are: blood at 37° C.=4-25 mPa·s, olive oil=~100 mPa·s, honey=2000-10000 mPa·s, chocolate syrup=10000-25000 mPa·s, molten chocolate=45000-130000 mPa·s, and peanut butter=~250000 mPa·s. The skilled person is well aware of how to determine the viscosity of a sample. For example, instruments for the measurement of viscosity, i.e., viscometers, are commercially available. A "viscous sample" in the context of the present invention means a material with a high viscosity, preferably a viscosity of at least $1 \times 10^4$ mPa·s, for example, tracheal or bronchial secretions, sputum, or blood-containing and purulent samples in general.

The term "untreated" in the context of the present invention means "unprocessed" or "raw". Thus, the expression "untreated bodily sample" means that the bodily sample is not treated by application of one or more chemical agent(s) or physical forces such as temperature or shearing forces, or any other procedures such as centrifugation, filtering, or sieving. For all aspects of the present invention, it is preferred that the bodily sample is untreated before it is contacted with the lysis buffer according to the present invention, the pre-mixed lysis composition, or before the first step of the methods according to the present invention is performed. However, in the event the bodily sample is stored for a certain period of time, for example, for more than 8 hours, before performing the methods of the present invention or before contacting the bodily sample with the lysis buffer according to the invention or the pre-mixed lysis composition, it is preferred that the bodily sample is stored at a temperature below 0° C., preferably below −5° C., more preferably below −10° C., and most preferably below −20° C. Thus, it is preferred that the only treatment of the bodily sample before performing the methods according to the present invention or before contacting the bodily sample with the lysis buffer according to the present invention or the pre-mixed lysis composition is freezing the sample.

A "nucleic acid isolation procedure" in the context of the present invention is a method that allows for isolation of nucleic acids from a complex mixture of substances and/or molecules such as a cell lysate. Preferably, the nucleic acid isolation procedure in the context of the present invention is a silica-based or magnetic bead technology. For example, a silica-based nucleic acid isolation procedure may be based on a silica membrane or on silica beads, preferably on a silica membrane. Nucleic acid isolation kits are commercially available, for example, the EZ-1 DNA Tissue Kit (ordering number 953034) or the QiaAmp™ DNA Blood Kit (ordering number 51104) from Qiagen. Depending on the nucleic acid isolation procedure or kit used it may be necessary to supplement the processed bodily sample with further reagents before performing the nucleic acid isolation procedure. For example, for nucleic acid isolation using silica membrane purifications, e.g., using the QiaAmp™ spin procedure from Qiagen, it is required to add ethanol (96-100%) to the lysed bodily sample according to the manufacturer's instructions before the mixture is transferred onto a QiaAmp™ spin column. Depending on the components used for lysis of the bodily sample, it may be preferable to add a mixture of Qiagen lysis buffer AL and ethanol (96 to 100%) to the lysed bodily sample, preferably to achieve a final volume ratio of bodily sample (including the components used for the lysis of the bodily sample other than Qiagen lysis buffer AL) to Qiagen lysis buffer AL to ethanol of approximately 1:1:1 prior to loading the mixture onto the silica membrane. Most preferably, the nucleic acid isolation procedure contemplated by the present invention does not involve extraction with organic solvents such as phenol and/or chloroform or precipitation with alcohol such as ethanol or isopropanol. The isolated nucleic acid is preferably 90%, more preferably 95%, most preferably 99% free of any other macromolecular structures such as proteins after performing the nucleic acid isolation procedure.

The term "heating" in the context of the present invention means "raising the temperature". Thus, "heating a mixture to a first temperature" means raising the temperature of a mixture to a defined temperature. For example, a mixture may be heated from room temperature to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60° C., or to any other temperature above 60° C. Preferably, "the first temperature" is in the range of 25 to 80° C., more preferably 30 to 60° C., most preferably the first temperature is 56±5° C. Preferably, the first temperature in the context of the present invention is a temperature at which a proteolytic enzyme, preferably the proteolytic enzyme used in the present invention is active. Preferably, the first temperature is the optimal reaction temperature for the proteolytic enzyme used in the present invention. Preferably, heating a mixture also includes keeping the mixture at the temperature it was heated to for a certain period of time. Preferably, "the second temperature" is higher than the first temperature. Preferably, the second temperature is in the range of 50 to 120° C., preferably 60 to 100° C., more preferably 80 to 100° C. For example, the second temperature may be 80, 81, 82, 83, 84, 85, 86, 87, 88, 89, 90, 91, 92, 93, 94, 95, 96, 97, 98, 99, or 100° C., preferably 96±5° C. Preferably, the term "heating to" a particular temperature also encompasses the term "incubating at" a particular temperature.

The term "bead milling" means agitation in the presence of beads. Thus, if a sample or mixture, preferably a liquid, viscous or semi-solid sample or mixture, is bead milled, the sample or mixture contains beads and the sample or mixture and the beads are agitated. Bead milling preferably results in homogenization of the sample or mixture and break up of cells due to the high liquid shear gradients and collision with the beads. The rate and effectiveness of the homogenization and cell lysis can be modified by changing the rates of agitation, the type of agitation movement, and/or the size of the beads, as well as the dimensions of the equipment. Preferably, the conditions of the bead milling step of the methods according to the present invention are such that one or more physical properties of the mixture is different before and after the bead milling step. Preferably, the mixture is more homogenous after bead milling, more preferably the mixture is less viscous after bead milling, for example, at least by a factor of 2, and most preferably the bead milling comprises lysis of cells present in the mixture, most preferably lysis of bacterial and/or yeast cells. The skilled person is well aware of bead milling procedures. For example, bead mills in various dimensions are commercially available.

A "nucleic acid amplification method" in the context of the present invention is any molecular biological technique that is suitable for amplifying, i.e., multiplying, a nucleic acid, wherein the amplification may be linear or exponential. Examples for nucleic acid amplification methods are polymerase chain reaction (PCR), nucleic acid sequence-based amplification (NASBA), ligase chain reaction (LCR), strand displacement amplification (SDA), multiple displacement amplification (MDA), Q-beta replicase amplification, and loop-mediated isothermal amplification. The amplification method may be specific for a certain nucleic acid such as a specific gene or a fragment thereof, or may be universal such that all or a specific type of a nucleic acid, such as mRNA, is amplified universally. For example, the skilled person may design oligonucleotide primers which specifically hybridize to the nucleic acid of interest and use these primers in a PCR experiment.

A "nucleic acid analysis method" in the context of the present invention is any method that allows for detection and/or identification of a specific nucleic acid, wherein the term "detection" also comprises the quantitative determination of a nucleic acid. The detection and/or identification may be based on specific amplification, for example, by the amplification of a specific DNA fragment using oligonucleotide primers specific for said DNA fragment in the polymerase chain reaction (PCR). The skilled person is well aware of how to design oligonucleotide primers which specifically hybridize to the nucleic acid of interest. The detection and/or identification may also be achieved without amplification, for example, by sequencing the nucleic acid to be analyzed or by sequence specific hybridization, for example, in the context of a microarray experiment. Sequencing techniques and microarray based analysis are well known procedures in the field.

The nucleic acid to be isolated, amplified, or detected and/or identified may be DNA, such as genomic DNA or cDNA, or RNA, such as messenger. RNA (mRNA) or ribosomal RNA (rRNA). Preferably, the nucleic acid is DNA. The skilled person is well aware of nucleic acid isolation, amplification, and analysis methods having regard to the general knowledge and the literature in the field.

The term "ready-to-use reaction tube" refers to pre-aliquoted reaction tubes that can be directly used for sample processing. This has the advantage that the reaction buffer does not have to be prepared and aliquoted before each use. In the context of the present invention, it is particularly preferred that the pre-mixed lysis composition is provided in a ready-to-use reaction tube. It is also preferred that the lysis buffer according to the present invention is provided in a ready-to-use reaction tube. Preferably, the tube can be securely closed such as a screw cap tube. Preferably, the tube, preferably the screw cap tube, has a volume in the range of 1 to 15 ml, preferably 1 to 2 ml, preferably 1.5 ml. A 1.5 ml tube is preferred, since it can be readily used with standard heating blocks. However, depending on the nature and amount of sample to be processed/analyzed the volume of the tube may be adjusted. Preferably, the tube contains a maximal amount of lysis buffer or pre-mixed lysis composition of ¼ of the volume of the tube, more preferably of ⅛ of the volume of the tube, wherein the volume of the lysis buffer and the pre-mixed lysis composition is determined without the volume of the beads.

The materials and processes described herein are suited for a one-tube-processing of biological samples such as bodily samples, in particular viscous bodily samples.

The term "one-tube-processing" means that all processing steps are performed in one tube, omitting the need for further handling steps. The phrase "in one tube" means according to the invention that the processed sample or a part thereof containing the desired material such as a nucleic acid material is not transferred from one vessel to another vessel during the processing steps. However, the term "tube" according to the invention is meant to include all reaction vessels of a suitable size and shape. Preferably, "one-tube-processing" in the context of the present invention means "one-tube-liquefaction", more preferably "one-tube-lysis", i.e., all processing steps up to liquefaction and/or lysis, respectively, are performed in one vessel. Most preferably, the thus processed material can be directly applied to subsequent procedures such as nucleic acid isolation, amplification, analysis and/or detection procedures.

An "automated process" in the context of the present invention means a process which is operated and/or controlled by automation. Preferably, an "automated process" in the context of the present invention does not require or include any manual handling steps. Thus, method steps that are performed in an automated process are preferably performed by an apparatus or device which is preferably programmable to perform said method steps in a sequential order.

A "pathogen" in the context of the present invention may be any organism that causes a disease in another organism. Preferably, a "pathogen" relates to an infectious organism such as a virus, a bacterium, protozoa, yeast, fungi, or a parasite. Preferably, the pathogen in the context of the present invention is a microorganism, such as a bacterium, yeast, fungi, or virus, more preferably a human pathogenic bacterium, yeast, fungi, or virus. Preferably, the pathogen is associated with a respiratory disease. The term "a pathogen associated with a respiratory disease" means a pathogen that usually appears in the context of a respiratory disease. For example, a pathogen associated with a respiratory disease may be the cause of a respiratory disease, however, it may also be an opportunistic pathogen which is indicative for a respiratory disease but is not the cause therefor. Preferably, a bacterium in the context of the present invention is of the family selected from the group consisting of Mycobacteriaceae (e.g., *Mycobacterium tuberculosis, Mycobacterium bovis, Mycobacterium africanum, Mycobacterium canetti, Mycobacterium caprae, Mycobacterium smegmatis*, and *Mycobacterium pinnipedii*), Pseudomonadaceae (e.g. *Pseudomonas aeruginosa*), Mycoplasmataceae (e.g., *Mycoplasma pneumoniae*), Chlamydiaceae (e.g., *Chlamydophila pneumoniae*), Enterobacteriaceae (e.g., *Klebsiella pneumoniae, Escherichia coli*), Staphylococcaceae (e.g., *Staphylococcus aureus*), Streptococcaceae (e.g., *Streptococcus pneumoniae*), Xantomonadaceae (e.g., *Stenotrophomonas maltophilia*), Moraxellaceae (e.g., *Moraxella catarrhalis, Acinetobacter baumannii, Acinetobacter* Legionellaceae (e.g., *Legionella pneumophila*), Burkholderiaceae (e.g., *Burkholderia cepacia*), Corynebacteriaceae (e.g., *Corynebacterium diphtheria*), Neisseriaceae (e.g., *Neisseria meningitis, Neisseria flavescens, Neisseria sicca*), Bacteroides (e.g., *Bacteroides fragilis*), and Pasteurellaceae (e.g., *Haemophilus influenzae*), preferably a yeast in the context of the present invention is of a family selected from the group consisting of Saccharomycetaceae (e.g., *Candida albicans*), Sporidiobolaceae (e.g., *Cryptococcus neoformans*), Trichocomaceae (e.g., *Aspergillus flavus, Aspergillus fumigatus*), and Pneumocystiaceae (e.g., *Pneumocystis jirovecii*).

Description

In a first aspect, the present invention relates to a lysis buffer comprising, preferably essentially consisting of, preferably consisting of (i) at least one chaotropic agent, (ii) at least one reducing agent, and (iii) at least one proteolytic enzyme. Preferably, the lysis buffer according to the invention further comprises beads. Thus, preferably the lysis buffer according to the present invention comprises, preferably essentially consists of, preferably consists of (i) at least one chaotropic agent, (ii) at least one reducing agent, (iii) at least one proteolytic enzyme, and (iv) beads. Preferably, said beads have a diameter in the range of about 300 μm to 800 μm, e.g., a diameter of 300 μm, 400 μm, 500 μm, 600 μm, 700 μm, or 800 μm, and preferably have a diameter of about 600 μm. Preferably, the beads are acid washed to dissolve or hydrolyze any contaminants that may be present on the untreated beads. For example, beads, preferably glass beads, may be acid washed by soaking them for at least one hour in 2 M $HNO_3$ and rinsing them with water until the rinse water is no longer acidic. Alternatively, acid washed glass beads may be obtained commercially, for example, from Sigma-Aldrich (ordering number G8772). Preferably, the beads, preferably the glass beads, are present in an amount in the range of about 200 to 1000 mg/ml, preferably 300 to 900 mg/ml, preferably 400 to 800 mg/ml. For example, the beads, preferably glass beads, are present in an amount of about 200 mg/ml, 300 mg/ml, 400 mg/ml, 500 mg/ml, 600 mg/ml, 700 mg/ml, 800 mg/ml, 900 mg/ml, or 1000 mg/ml, most preferably in an amount of about 550 mg/ml. For example, 140 mg of glass beads may be added to 250 μl of lysis buffer to obtain an amount of 560 mg/ml glass beads in the lysis buffer (thus, the volume of the glass beads is not taken into account). Preferably, the beads, preferably the glass beads, are suitable for bead milling.

Preferably, the nature and concentration of the at least one chaotropic agent and the at least one reducing agent are chosen such that the at least one proteolytic enzyme is active.

In a preferred embodiment, the nature and concentration of the chaotropic agent and/or the nature and concentration of the reducing agent and/or the nature and concentration of the proteolytic enzyme is such that liquefaction, preferably lysis, of a bodily sample is achieved when the lysis buffer is mixed with the sample, wherein preferably the bodily sample is as defined above. In a preferred embodiment, the nature and concentration of the chaotropic agent and/or the nature and concentration of the reducing agent and/or the nature and concentration of the proteolytic enzyme is such that the lysis buffer is suitable for the lysis of at least 2 different types of bodily samples, preferably such that the lysis buffer is universally applicable.

It is particularly preferred that the lysis buffer according to the present invention is universally applicable for the lysis of bodily samples that are relevant for the diagnosis of a respiratory disease, such as blood, punctates, drainages, sputum, pus, pleural fluid, pleural punctates, bronchial secretion, tracheal secretion, endotracheal secretion, bronchial aspirates, tracheal aspirates, endotracheal aspirates, bronchial lavage, bronchoalveolar lavage (BAL), bronchial swab, nasopharyngeal swab, laryngeal swab, gastric juice, gastric aspirates, and lung biopsies. Preferably, the lysis buffer according to the present invention is universally applicable for the lysis of bodily samples. Preferably, the lysis buffer according to the present invention is universally applicable, preferably as defined above.

Preferably, in the lysis buffer according to the present invention, the chaotropic agent is guanidinium thiocyanate, guanidinium isothiocyanate, guanidinium hydrochloride, guanidinium chloride, alkali thiocyanate, alkali isothiocyanate, alkali iodide, or alkali perchlorate, wherein the alkali ion is preferably potassium or sodium. More preferably, the chaotropic agent is selected from the group consisting of guanidinium hydrochloride, guanidinium thiocyanate, and guanidinium isothiocyanate, wherein most preferably the chaotropic agent is guanidinium hydrochloride or guanidinium thiocyanate. The skilled person will recognize that more than one chaotropic agent may be combined in the lysis buffer according to the present invention. For example, guanidinium hydrochloride and guanidinium thiocyanate may be combined. In one embodiment, the chaotropic agent in the sense of the present invention is a commercially available lysis buffer which contains as a component a chaotropic agent, preferably as a main component. In this context, "main component" means that the buffer contains, besides water, primarily the chaotropic agent. An example for such a commercially available lysis buffer that is considered a chaotropic agent in the context of the lysis buffer according to the present invention is the Qiagen lysis buffer AL (Qiagen ordering number 19075) which contains guanidinium hydrochloride.

In a preferred embodiment, the chaotropic agent or the combination of chaotropic agents is present in a concentration in the range of 0.2 M to 8.0 M, preferably in the range of 1.0 M to 7.0 M, more preferably in the range of 2.0 M to 6.0 M, most preferably in the range of 2.5 M to 5.2 M. For example, the at least one chaotropic agent, preferably guanidinium hydrochloride, may be present in a concentration of 0.2 M, 0.5 M, 0.8 M, 1.0 M, 1.5 M, 2.0 M, 2.5 M, 3.0 M, 3.5 M, 4.0 M, 4.5 M, 5.0 M, 5.5 M, 6.0 M, 6.5 M, 7.0 M, 7.5 M, or 8.0 M, preferably in a concentration of more than 3.0 M, preferably in a concentration of more than 4.0 M, even more preferably between 5.0 M and 6.0 M, and most preferably in a concentration of 5.5 M. The skilled person will recognize that the optimal concentration of the chaotropic agent in the lysis buffer according to the present invention will depend on the nature of the chaotropic agent, the sample to be processed, and/or the proteolytic enzyme used and may be adjusted based on the chaotropic agent or the combination of chaotropic agents used. For example, if the chaotropic agent is guanidinium thiocyanate the concentration of the chaotropic agent is preferably in the range of 0.2 M to 2.0 M, more preferably 0.2 M to 1.5 M, e.g., 0.2 M, 0.3 M, 0.4 M, 0.5 M, 0.6 M, 0.7 M, 0.8 M, 0.9 M, 1.0 M, 1.1M, 1.2 M, 1.3 M, 1.4 M, or 1.5 M. The most preferred chaotropic agents are guanidinium hydrochloride and guanidinium thiocyanate.

As described above, the chaotropic agent contained in the lysis buffer according to the present invention may be provided by a commercially available lysis buffer. In this context, the commercially available lysis buffer as described above is present in the lysis buffer according to the present invention preferably to at least 50% (vol/vol), preferably to at least 60% (vol/vol), preferably to at least 70% (vol/vol), preferably to at least 80% (vol/vol), more preferably to at least 85% (vol/vol), even more preferably to at least 90% (vol/vol), and most preferably to at least 95% (vol/vol), and is most preferably the Qiagen lysis buffer AL.

Preferably, the reducing agent is selected from the group consisting of dithiothreitol (DTT), N-acetyl-cysteine (NALC), beta-mercaptoethanol, Tris(2-Carboxyethyl) phosphine (TCEP), and thioredoxin. Preferably, the reducing agent is NALC or DTT, most preferably DTT. A combination of more than one reducing agent is also contemplated. The reducing agent or combination of reducing agents are preferably present in the lysis buffer in a concentration in the range of 1.0 mM to 200 mM, preferably in the range of 5.0 mM to 100 mM, more preferably in the range of 20 mM to 60 mM. For example, the at least one reducing agent, preferably DTT, may be present in the lysis buffer according to the present invention in a concentration of 1.0 mM, 5.0 mM, 10 mM, 15 mM, 20 mM, 25 mM, 30 mM, 40 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM, preferably the concentration is above 20 mM, preferably the concentration is about 40±10 mM, more preferably about 40 mM. However, the skilled person will recognize that the concentration of the reducing agent in the lysis buffer according to the present invention will depend on the nature of the reducing agent, the sample to be processed, and/or the proteolytic enzyme used and may be adjusted based on the reducing agent or combination of reducing agents used.

Preferably, the proteolytic enzyme in the lysis buffer according to the present invention is as described above. Preferably, the proteolytic enzyme is present in a concentration in the range of 10 to 200 units/ml, preferably in the range of 20 to 100 units/ml, more preferably in the range of 30 to 70 units/ml, more preferably in the range of 40 to 60 units/ml. For example, the proteolytic enzyme, preferably proteinase K, may be present in the lysis buffer according to the present invention in a concentration of about 10, 15, 20, 25, 30, 35, 40, 45, 50, 55, 60, 65, 70, 75, 80, 85, 90, 95, or 100 units/ml, preferably in a concentration of 50±20 units/ml, most preferably in a concentration of 50±5 units/ml, wherein preferably the unit definition is as described above for proteinase K. The most preferred proteolytic enzyme is proteinase K. Proteinase K is a stable protease with broad substrate specificity which is highly active even in the presence of chaotropic and reducing agents, tolerates a wide range of pH levels and buffer conditions, and has an optimal activity at a working temperature of 56° C.

It is particularly preferred that the lysis buffer according to the present invention does not contain any other enzyme than the at least one proteolytic enzyme.

In one embodiment, the lysis buffer according to the present invention does not contain a detergent, in particular, it is preferred that the lysis buffer according to the present invention does not contain any of SDS, N-lauroyl-sarcosine, Tween 20, Tween 80, and Triton-X-100. In one embodiment, the lysis buffer according to the present invention does not contain a chelating agent, in particular, it is preferred that the lysis buffer does not contain EDTA or EGTA. In one embodiment, the lysis buffer does not contain (i) an enzyme other than the at least one proteolytic enzyme, (ii) a detergent, and (iii) a chelating agent.

In a preferred embodiment, the lysis buffer has a pH that is approximately neutral. In a preferred embodiment, the lysis buffer has a pH in the range of 5.5 to 8, i.e., a pH of 5.5, 6, 6.5, 7, 7.5, or 8, preferably a pH of around 7. The lysis buffer according to the present invention may comprise buffering components that may, for example, be used to adjust the pH of the lysis buffer. Examples for such buffering components include, for example, 3-{[tris(hydroxymethyl) methyl]amino}propanesulfonic acid (TAPS), N,N-bis(2-hydroxy-ethyl)glycine (Bicine), tris(hydroxymethyl)methylamine (TRIS), N-tris(hydroxylmethyl)-methylglyxine (Tricine), 4-2-hydroxyethyl-1-piperazineethanesulfonic acid (HEPES), 2-{[tris(hydroxymethyl)methyl] amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate), saline sodium citrate (SSC), and 2-(N-morpholino)ethanesulfonic acid (MES).

In a preferred embodiment, the lysis buffer according to the present invention comprises, preferably essentially consists of, preferably consists of a chaotropic agent in a concentration in the range of 2 to 6 M, preferably 2 to 5 M, preferably 2.3 to 4.7 M, a reducing agent in a concentration in the range of 25 to 75 mM, preferably about 50 mM, a proteolytic enzyme in a concentration in the range of 20 to 100 units/ml, preferably about 50 units/ml, and optionally beads, preferably glass beads, of a diameter in the range of 500 to 700 µM, preferably about 600 µM, in a concentration in the range of 500 to 700 mg/ml, preferably about 600 mg/ml. Preferably, the chaotropic agent is guanidinium hydrochloride and/or the reducing agent is DTT and/or the proteolytic enzyme is proteinase K. Preferably, the beads, preferably glass beads, are present in the lysis buffer.

In a particularly preferred embodiment of the lysis buffer according to the present invention, the lysis buffer comprises, preferably essentially consists of, preferably consists of 80 to 95% (vol/vol) Qiagen lysis buffer AL, 3 to 7% (vol/vol) 1M DTT, 6 to 14% (vol/vol) 20 mg/ml (>600 mAU/m) proteinase K, and optionally glass beads, preferably the lysis buffer consists of about 88% (vol/vol) Qiagen lysis buffer AL, about 4% (vol/vol) 1 M DTT, and about 8% (vol/vol) 20 mg/ml (>600 mAU/ml) proteinase K to which glass beads may or may not be added. For example, 230 µl±5 µl Qiagen lysis buffer AL, 10 µl±2 µl 1 M DTT, 20 µl±4 µl, and optionally 140 mg±20 mg glass beads of about 600 µm diameter may be mixed for producing the lysis buffer according to the present invention, wherein preferably the glass beads are added.

In a preferred embodiment, the lysis buffer according to the present invention is provided in a ready-to-use reaction tube. In this embodiment, the proteolytic enzyme is preferably separated from the chaotropic and the reducing agent. For example, the proteolytic enzyme may be present in the ready-to-use reaction tube as dried spot on the inside of the cap or lid of the tube, for example, on the inside of a screw cap.

A second aspect of the present invention relates to the use of (i) at least one chaotropic agent, (ii) at least one reducing agent, and (iii) at least one proteolytic enzyme for the lysis of a broad spectrum of bodily samples. Preferably, the lysis in this context encompasses the provision of a lysis reaction mixture as described above in the definitions. Thus, it is particularly preferred that the at least one chaotropic agent, the at least one reducing agent, and the at least one proteolytic enzyme is used for the lysis as defined above for the lysis reaction mixture.

Preferably, the at least one chaotropic agent, the at least one reducing agent, and the at least one proteolytic enzyme are as described above, e.g., in the definitions and for the lysis buffer of the first aspect of the present invention. Preferably, the bodily samples are as described above.

In this aspect of the present invention, two or more of the at least one chaotropic agent, the at least one reducing agent, and the at least one proteolytic enzyme may be present in a composition, for example, in a composition comprising the at least one chaotropic agent and the at least one reducing agent, preferably lacking the at least one proteolytic enzyme. In a preferred embodiment, said composition is the pre-mixed lysis composition as described above in the definitions. In another embodiment, the composition is the lysis buffer according to the first aspect of the present invention. The composition is preferably present in a ready-to-use reaction tube. The bodily sample, and if applicable also the proteolytic enzyme, is preferably added to the ready-to-use reaction tube and lysis is preferably performed in said tube. Preferably, the entire lysis happens in a single tube, such that further handling steps that may be accompanied by the risk of contamination are omitted.

In one embodiment, the at least one chaotropic agent, the at least one reducing agent, and the at least one proteolytic enzyme are present in a composition. Preferably, said composition is the lysis buffer according to the first aspect of the present invention. In this embodiment, said composition is preferably used as broad-spectrum lysis buffer, i.e., as universally applicable lysis buffer, which is preferably suitable for, preferably applied for, the lysis of two or more, such as 2, 3, 4, 5, 6, 7, 8, 9, 10 or more different types of bodily samples, preferably the bodily samples are relevant for the diagnosis of a respiratory disease, such as blood, sputum, pus, pleural fluid, pleural punctates, bronchial secretion, tracheal secretion, endotracheal secretion, bronchial aspirates, tracheal aspirates, endotracheal aspirates, bronchial lavage, bronchoalveolar lavage (BAL), bronchial swab, nasopharyngeal swab, laryngeal swab, gastric juice, gastric aspirates, and lung biopsies. Preferably, the different types of bodily samples are as described above.

Thus, the present invention provides the use of a composition comprising (i) at least one chaotropic agent, (ii) at least one reducing agent, and (iii) at least one proteolytic enzyme as broad-spectrum lysis buffer, preferably for bodily samples.

It is particularly preferred that the bodily samples are untreated or only frozen before the composition is used as broad-spectrum lysis buffer.

It is particularly preferred that, after lysis, the bodily sample is suitable for being directly applied to a nucleic acid isolation procedure, such as silica- or magnetic bead technology-based nucleic acid isolation procedures, without the need for further processing such as extraction with organic solvents or precipitation before application to the nucleic acid isolation procedure. However, depending on the nucleic acid isolation procedure, it may be necessary to supplement the lysed bodily sample with further reagents as described above. For example, commercially available nucleic acid isolation kits, such as the EZ-1 DNA Tissue Kit (magnetic bead technology) or the QiaAmp™ DNA Blood Kit (silica membrane based) from Qiagen, may be used in the context of the present invention. For EZ-1 nucleic acid isolation, the lysed bodily sample is preferably directly placed into the BioRobot® EZ-1 workstation and further processing is performed according to the manufacturer's instructions. For QiaAmp™ nucleic acid isolation, preferably ethanol (96-100%) is added to the lysed bodily sample according to the manufacturer's instructions and the mixture is transferred onto a QiaAmp™ spin column. Depending on the components used for lysis of the bodily sample, it may be preferable to add a mixture of Qiagen lysis buffer AL and ethanol (96 to 100%) to the lysed bodily sample, preferably to achieve a final volume ratio of bodily sample (including the components used for the lysis of the bodily sample other than Qiagen lysis buffer AL) to Qiagen lysis buffer AL to ethanol of approximately 1:1:1 prior to loading the mixture onto the silica membrane. Further process steps are then performed as recommended by the manufacturer. Alternatively to the silica membrane-based isolation using a centrifuge a vacuum based application may be used. Preferably, an underpressure of at least 400 mbar, more preferably at least 600 mbar, and most preferably at least 800 mbar is applied for binding and washing steps in this experimental setup.

In this aspect of the present invention, the lysis of each of the broad spectrum of bodily samples is preferably performed as described for the method of the third aspect of the present invention, preferably, using for each of the broad spectrum of bodily samples an essentially identical embodiment of the method according to the third aspect of the present invention.

In a particularly preferred embodiment, the use is for high-throughput lysis of a broad spectrum of bodily samples.

In a third aspect, the present invention provides a method for processing a bodily sample comprising the step of (i) providing a mixture comprising the bodily sample to be processed, at least one chaotropic agent, at least one reducing agent, and at least one proteolytic enzyme. Preferably, the components of the mixture are as described above, e.g., in the definitions and for the first aspect of the present invention. Preferably, said mixture is the lysis reaction mixture as described above in the definitions. Thus, preferably, step (i) of the method according to the third aspect is providing a lysis reaction mixture as defined above in the definitions.

Preferably, the method according to the third aspect of the present invention further comprises the step of (ii) heating the mixture to a first temperature. Preferably, the method according to the third aspect of the present invention further comprises the step of (iii) heating the mixture to a second temperature. Preferably, the method according to the third aspect of the present invention further comprises the step of (iv) bead milling the mixture.

Preferably, the method according to the third aspect of the present invention is universally applicable to bodily samples, preferably to bodily samples relevant for the diagnosis of a respiratory disease. Preferably, the method according to the third aspect of the present invention is applicable to, preferably applied to a broad spectrum of bodily samples. Preferably, the method is for processing, preferably lysing, a broad spectrum of bodily samples.

Preferably, the method according to the third aspect of the present invention comprises steps (i), (ii), (iii), and (iv), preferably in this sequential order. However, in the method according to the third aspect of the present invention, one or more of the steps (ii), (iii), and (iv) may be omitted. For example, the method according to the third aspect of the present invention may comprise steps (i), (ii), and (iv), or steps (i), (iii), and (iv), or steps (i), (ii), and (iii), or steps (i) and (ii), or steps (i) and (iii), or steps (i) and (iv). Furthermore, the individual steps may be repeated. For example, the method according to the third aspect of the present invention may comprise the following steps in this sequential order: step (i), (iv), (ii), (iv), (iii), (iv), (iii), and (iv), wherein two or more of the steps may be performed simultaneously and/or one step may be performed during another step. For example, it is preferred that step (iv) is performed one or more times, e.g., 1, 2, or 3 times, during step (iii). It is also preferred that step (iv) is performed for mixing the bodily sample with the lysis buffer in step (i). Furthermore, it is preferred that step (iv) is performed between steps (ii) and (iii).

Step (i) preferably comprises the steps (a) contacting (in the sense of "bringing together") the components of the mixture and (b) mixing the components of the mixture, preferably such that a uniform mixture is achieved. The components may be contacted and mixed in any possible combination of the individual components.

For example, this also includes the possibility that a subset of components of the mixture are $(a_1)$ contacted and preferably $(b_1)$ mixed, and then one or more remaining components are $(a_2)$ contacted with the mixture of $(b_1)$ and then $(b_2)$ mixed until all components of the mixture are contacted and mixed, or that two or more components of the mixture are $(a_1)$ contacted and $(b_1)$ mixed and that other two or more components are $(a_2)$ contacted and $(b_2)$ mixed, and then the mixtures of $(b_1)$ and $(b_2)$ are $(a_3)$ contacted and $(b_3)$ mixed until all components of the mixture are contacted and mixed etc.

For example, in step (i), (1) all components of the mixture may be contacted and preferably mixed, e.g., by adding all components to a reaction tube in any possible sequential order and then mixing the components in the reaction tube, or (2) all components of the mixture except of the bodily sample may be contacted and preferably mixed, and then the bodily sample is contacted and preferably mixed with the other pre-contacted and preferably pre-mixed components, or (3) all components of the mixture except of the bodily sample and the at least one proteolytic enzyme are contacted and preferably mixed, and then the bodily sample is contacted and preferably mixed with the pre-contacted and preferably pre-mixed components, and then the at least one proteolytic enzyme is contacted and preferably mixed with the remaining pre-contacted and preferably pre-mixed components, or (4) all components of the mixture except of the bodily sample and the at least one proteolytic enzyme are contacted and preferably mixed, the bodily sample and the proteolytic enzyme are contacted and preferably mixed, and then the pre-contacted and preferably pre-mixed components are contacted and preferably mixed etc.

In the above example variant (1), it is possible that all individual components are added separately, e.g., to a reaction tube, and are mixed. For example, the individual components of the mixture may be added individually to the bodily sample to be processed.

In the above example variant (2), the mixture of all components of the mixture except of the bodily sample is preferably a composition comprising at least one chaotropic agent, at least one reducing agent, and at least one proteolytic enzyme, and is preferably the lysis buffer according to the first aspect of the present invention.

In the above example variants (3) and (4), the mixture of all components of the mixture except of the bodily sample and the at least one proteolytic enzyme is preferably a composition comprising at least one chaotropic agent and at least one reducing agent, and is preferably the pre-mixed lysis composition as described above in the definitions.

The above example variant (3) is a particularly preferred embodiment of the method according to the third aspect of the present invention.

In those embodiments, where some of the components of the mixture are provided as a pre-contacted and preferably pre-mixed composition, such composition is preferably provided in one or more reaction tubes, preferably ready-to-use reaction tubes. In these embodiments, the bodily sample may be directly added to the reaction tube, preferably the ready-to-use reaction tube, without having to prepare and aliquot the lysis buffer or having to add each buffer component individually to the sample. The optionally lacking components such as the proteolytic enzyme may, for example, be added together with the bodily sample or before or subsequently to the bodily sample.

In a particularly preferred embodiment of the third aspect of the present invention, in step (i) the bodily sample is contacted and preferably mixed with a pre-mixed composition comprising a subset of components of the mixture and then the remaining components of the mixture are contacted and preferably mixed with the mixture of the bodily sample and the pre-mixed composition. It is particularly preferred that the pre-mixed composition comprising a subset of components of the mixture comprises at least one chaotropic agent and at least one reducing agent, but does not contain the at least one proteolytic enzyme. Preferably the pre-mixed composition comprises all components of the mixture except of the proteolytic enzyme and the bodily sample. It is particularly preferred that this pre-mixed composition is the pre-mixed lysis composition as described above.

In this embodiment, the bodily sample to be processed is preferably contacted with the pre-mixed composition preferably comprising the at least one chaotropic agent and the at least one reducing agent (without proteolytic enzyme), preferably the pre-mixed lysis composition as described above, in step (i), preferably in a volume ratio of bodily sample to pre-mixed composition in the range of 0.5:1 to 1:2, e.g., in a ratio of 0.5:1, 0.6:1, 0.7:1, 0.8:1, 0.9:1, 1:1, 1:1.2, 1:1.4, 1:1.6, 1:1.8, or 1:2, preferably 1:1.1, wherein if the pre-mixed composition contains beads the volume of the beads is not considered for the volume of the pre-mixed composition. For example, 220 μl±30 μl of a bodily sample to be processed, more preferably of an untreated bodily sample, is added to 240 μl±30 μl of pre-mixed lysis composition (for example, consisting of 230 μl±25 μl Qiagen lysis buffer AL and 10 μl±3 μl 1 M DTT), optionally containing 140 mg±20 mg beads, preferably glass beads, preferably with a diameter of about 600 μm. The composition is preferably mixed. The at least one proteolytic enzyme may be contacted with the composition before, during, or after mixing. For example, the at least one proteolytic enzyme may be added during mixing if the at least one proteolytic enzyme is provided as a dried spot in the lid of the reaction tube and the composition is contacted with the lid of the reaction tube during mixing. The at least one proteolytic enzyme may also be added before or after mixing, e.g., as a solution. In the above example, e.g., 20 μl of 20 mg/ml (>600 mAU/ml) may be added.

In the embodiment, in which the bodily sample is contacted with the lysis buffer according to the first aspect of the present invention in step (i), the bodily sample is preferably contacted with the lysis buffer in a volume ratio of bodily sample to lysis buffer in the range of 0.5:1 to 1:2, e.g., in a ratio of 0.5:1, 0.6:1, 0.7:1, 0.8:1, 0.9:1, 1:1, 1:1.2, 1:1.4, 1:1.6, 1:1.8, or 1:2, preferably 1:1.2, wherein the volume of the optional beads is not considered for the volume of the lysis buffer. For example, 250 μl±30 μl of lysis buffer, optionally containing 140 mg±20 mg beads, preferably glass beads, preferably with a diameter of about 600 μm, are contacted with 220 μl±30 μl of a bodily sample, more preferably an untreated bodily sample.

The skilled person will recognize that the exact aliquot amounts of a bodily sample, in particular of a viscous bodily sample, such as a sputum sample or tracheal secretion sample, can be difficult to achieve if the specimens are very mucous, however, the system is not sensitive to some variation in sample input amount, thus, the variation in the sample volume may be higher.

Preferably, the bodily sample is mixed with the other components of the mixture in step (i) such that a good contact between all components of the mixture is guaranteed. The skilled person is well aware of how to achieve a thorough mixture of a bodily sample, in particular a viscous bodily sample, with the other components of the mixture. For example, the bodily sample may be contacted with the other components of the mixture, for example, with a pre-mixed composition of certain components of the mixture as described above, and is then mixed by vortexing or pipetting up and down. For example, the mixture may be mixed by vortexing, preferably vigorously, e.g., for several seconds up to one to two minutes. The mixture may also be mixed by applying step (iv). If pipetting up and down is used, it may be advisable to use pipette tips which have a wide opening, for example, pipette tips of which the very tip has been cut off. In a preferred embodiment, the mixture of step (i) is incubated for a time period in the range of 1 minute to 1 hour, e.g., 1, 5, 10, 15, 20, 25, 30, 40, 50, or 60 minutes, preferably at around room temperature, e.g., at 18, 20, 22, 24, or 26° C. The incubation time depends on whether steps (ii) and/or (iii) and/or (iv) are performed. The skilled person will recognize that when omitting step (ii), (iii), and/or (iv) the incubation time may be longer, for example, 60 minutes.

Preferably, in step (ii) the mixture is heated to a first temperature at which the proteolytic enzyme is preferably active. For example, if the proteolytic enzyme is proteinase K, the first temperature is preferably in the range of 45 to 60° C., preferably 50 to 60° C., more preferably 54 to 58° C., and most preferably the first temperature is about 56±1° C. Preferably, the mixture is kept at the first temperature, preferably, for a period of time which allows the proteolytic enzyme to act on proteins in the bodily sample, such as for a time period in the range of 5 to 60 minutes, e.g., 5, 10, 15, 20, 25, 30, 35, 40, 45, 50, 55, or 60 minutes, preferably at least 10 minutes. The skilled person will be aware that the incubation time to achieve a certain proteolytic result may have to be adjusted to the buffer and temperature conditions. For example, if a suboptimal temperature is used and/or the lysis buffer contains components which inhibit the activity of the proteolytic enzyme the incubation time is ideally extended.

Preferably, the mixture is heated in step (iii) to a sufficient temperature and/or for a sufficient time to cause liquefaction of the sample, more preferably to cause lysis of the sample, i.e., lysis of the cells present in the sample. Preferably, the mixture is heated in step (iii) to a sufficient temperature and/or for a sufficient time to cause solubilization of viscous and solid components in the sample. Preferably, heating step (iii) comprises inactivation of the cells in the sample, in particular, inactivation of microorganisms, such as bacterial and/or yeast cells. Preferably, mycobacteria are inactivated by heating step (iii). The skilled person can easily determine a suitable temperature and duration of heating to cause liquefaction and/or lysis by simple experiments determining the viscosity of the samples and/or the number of intact or viable cells before and after heating treatments under varying conditions, i.e., varying temperatures and time periods. For example, the samples may be heated to 80° C. for 5 minutes, 85° C. for 5 minutes, 90° C. for 5 minutes, 95° C. for 5 minutes, 98° C. for 5 minutes, 80° C. for 10 minutes, 85° C. for 10 minutes, 90° C. for 10 minutes, 95° C. for 10 minutes, 98° C. for 10 minutes, 80° C. for 15 minutes, 85° C. for 15 minutes, 90° C. for 15 minutes, 95° C. for 15 minutes, or 98° C. for 15 minutes, and the viscosity and/or the number of intact or viable cells may be determined before and after the heating step. The skilled person will recognize that the optimal heating temperature and heating duration depends on the nature of the sample used. It is particularly preferred that the heating step (iii) comprises lysis of at least part of the cells, preferably all cells present in the sample. Most preferably, after heating step (iii), no viable cells, most preferably no viable mycobacteria, in particular no viable *M. tuberculosis*, is present in the mixture. The skilled person is well aware of how to determine whether viable bacteria are present in the mixture, for example, by cultivation tests. Preferably, the mixture is heated in step (iii) to a temperature in the range of 80° C. to 99° C., e.g., to 80° C., 85° C., 90° C., 92° C., 94° C., 95° C., 96° C., 97° C., 98° C., or 99° C., more preferably the mixture is heated to at least 90° C., most preferably to about 96° C. Preferably, the mixture is kept at the temperature it was heated to, preferably for a time period in the range of 5 to 30 minutes, e.g., for 5, 10, 15, 20, 25, or 30 minutes, more preferably for at least 10 minutes, most preferably for at least 15 minutes. In a particularly preferred embodiment of the third aspect of the present invention, the mixture is heated to 96° C.±5° C., preferably to 96° C.±1° C., and kept at this temperature for 15 minutes. The skilled person will recognize that any combination of temperatures and time periods is contemplated by the present invention as long as the above described effects are achieved. For example, the samples may be heated to 90° C. for 5 minutes, 90° C. for 10 minutes, 90° C. for 15 minutes, 90° C. for 20 minutes, 90° C. for 25 minutes, 90° C. for 30 minutes, 96° C. for 5 minutes, 96° C. for 10 minutes, 96° C. for 15 minutes, 96° C. for 20 minutes, 96° C. for 25 minutes, or 96° C. for 30 minutes etc.

Preferably, the conditions of the bead milling step (iv) of the method according to the third aspect of the present invention are such that one or more physical properties of the mixture is different before and after the bead milling step. Preferably, the mixture is more homogenous after bead milling, more preferably the mixture is less viscous after bead milling, for example, at least by a factor of 2, and most preferably the bead milling comprises lysis of cells present in the mixture, most preferably lysis of bacterial and/or yeast cells. Preferably, the beads used for the bead milling procedure in step (iv) of the method according to the third aspect of the present invention have a diameter in the range of about 300 μm to 800 μm, e.g., a diameter of 300 μm, 400 μm, 500 μm, 600 μm, 700 μm, or 800 μm, and preferably have a diameter of about 600 μm. Preferably, the beads, preferably the glass beads, are acid washed to dissolve or hydrolyze any contaminants as described for the first aspect of the present invention. Preferably, the mixture containing the beads, preferably the glass beads, is agitated at a speed in the range of 1500 to 3500 rpm, e.g., 1500, 1750, 2000, 2250, 2500, 2750, 3000, 3250, 3500 rpm, most preferably at a speed of 2000±100 rpm, preferably for a time period of at least 2 minutes, preferably of at least 5 minutes, preferably using a standard vortex such as an IKA vortex. Alternatively or in addition to a vortex, a bead miller may be used for bead milling. The bead miller is preferably operated at a milling speed relating to an acceleration in the range of 50 to 200 g, preferably 50 to 100 g, preferably about 100 g, preferably for 2 to 10 minutes, preferably 3 to 8 minutes, preferably about 5 minutes. Preferably, the bead milling step is performed at an elevated temperature, for example, at a temperature above 40° C., preferably above 50° C., preferably above 60° C., preferably above 70° C., more preferably above 80° C., more preferably above 90° C., and most preferably the bead milling step is performed at about 96° C.

In a preferred embodiment, the bead milling step (iv) is performed parallel to the heating step (ii) or (iii), preferably parallel to the heating step (iii). The expression "one step is performed parallel to the other", for example, may mean that the one step is performed simultaneously to the other or that the one step is performed during the other, wherein "simultaneously" preferably means that both steps are performed for the same period of time and simultaneously and wherein "during" preferably means that a shorter step is performed at least once, such as once, 2, 3, 4, 5, 6, 7, 8, 9, 10, or more times during a longer step. Thus, it is particularly preferred that step (iv) is performed simultaneously to or at least once, preferably twice, during step (ii) or (iii). For example, step (iii) may be performed for 15 minutes, e.g., the mixture may be heated to 96° C.±5° C., preferably to 96° C.±1° C., for 15 minutes, and step (iv) may be performed once, preferably twice, for preferably at least 1 minute, preferably at least 2 minutes, preferably at least 3 minutes, preferably at least 5 minutes, up to 15 minutes during step (iii). For example, the shorter step may be started at the beginning of the longer step, the shorter step may be started after the longer step has been started and may be terminated before the longer step is finished, or the shorter step may be started such that it is finished together with the longer step. Preferably, the shorter step is started at the beginning of the longer step, preferably when the target temperature of the longer step has been reached.

In a particularly preferred embodiment of the method according to the third aspect of the present invention, steps (i), optionally (ii), optionally (iii), and optionally (iv), for example, in this sequential order, are performed in a single tube without the need of transferring supernatants or other handling steps requiring the removal of the sample/mixture from the reaction tube. Thus, preferably, the method according to the third aspect of the present invention is a "one-tube-processing" method. Preferably, these steps (i), optionally (ii), optionally (iii), and optionally (iv) of the method according to the third aspect of the present invention are performed in a ready-to-use reaction tube.

In a preferred embodiment of the method according to the third aspect of the present invention, steps (ii) to (iv), preferably steps (i)(b), i.e., mixing the components of the mixture, to (iv) are performed in an automated process. Thus, it is particularly preferred that mixing the components of the mixture of step (i), optionally (ii) heating the mixture to a first temperature, optionally (iii) heating the mixture to a second temperature, and optionally (iv) bead milling the mixture is performed fully automated in a single tube by a device, thus, rendering any manual handling steps, apart from step (i)(a) contacting the components of the mixture, dispensable, and thus, reducing the risk of contamination. Preferably, the device is programmable to perform the desired steps in any sequential order and/or to repeat one or more of the steps. An example of an automated method according to the present invention is shown in FIG. 2. Generally, all the features of the method steps described above are also applicable to the automated process. The automation of the method according to the third aspect of the present invention is highly advantageous providing best lysis efficiencies and reduced process times and would not be possible without the present invention, since only the present invention provides the opportunity to perform a full lysis of a bodily sample in a single tube, i.e., in a one-tube-process. The automated process is particularly preferred for samples which are suspected to contain highly pathogenic organisms such as mycobacteria, e.g., *M. tuberculosis*.

In a preferred embodiment of the third aspect of the present invention, the method comprises the liquefaction of the bodily sample, in particular of a viscous bodily sample such as sputum or tracheal secretion. Preferably, the method according to the third aspect of the present invention comprises the lysis of the cells present in the sample, most preferably lysis and inactivation of pathogens, in particular of mycobacteria, present in the sample. Preferably, the bodily sample, is not treated, in particular not cleared or decontaminated, before step (i). This means that the bodily sample is not treated with any agents such as DTT or NALC or a combination of these reagents to clarify/liquefy the sample or with SDS, NaOH, NALC, or a combination of these reagents to decontaminate the sample before step (i). "Decontamination" preferably means that any organisms other than mycobacteria, in particular, *M. tuberculosis*, such as bacteria, yeast or host flora, is inactivated before the mixture is cultured to detect the presence of mycobacteria in the sample. However, even though the method of the third aspect of the present invention is contemplated for bodily samples which have not been decontaminated before step (i), preferably which have not been treated before step (i), it is emphasized that the method is also suitable for decontaminated or otherwise pre-treated bodily samples.

In a preferred embodiment, the bodily sample is untreated before performing step (i) of the method according to the third aspect of the present invention. In another embodiment, the bodily sample is frozen before performing step (i) of the method according to the third aspect of the present invention, however, preferably the method does not comprise any treatment steps before step (i) other than freezing the sample. Thus, in a preferred embodiment, the only treatment of the bodily sample before performing step (i) is freezing the sample.

In a particularly preferred embodiment of the third aspect of the present invention, the mixture is heated in steps (ii) and (iii) as described above and bead milled in step (iv) as described above. For example, the mixture may be heated to 56±3° C. for 10 to 20 minutes, preferably for 10 minutes in step (ii), to 96±5° C. for 10 to 20 minutes, preferably for 15 minutes in step (iii), and then bead milled at 2000±100 rpm or 100±10 g for at least 5 minutes in step (iv). Any other combination of the above described heating and bead milling conditions is also contemplated. However, it is emphasized that the method according to the third aspect of the present invention may omit any or both of the heating steps (ii) or (iii) and/or the bead milling step (iv). The skilled person will recognize that if one or more of the steps (ii), (iii), and (iv) is/are omitted the mixture of step (i) is preferably incubated for a sufficient time to cause changes in one or more physical properties of the sample, preferably decreasing viscosity, for example, at least by a factor of 2, and most preferably for a sufficient time to cause lysis and/or inactivation of pathogens present in the sample. As described above, the skilled person is well aware of how to determine such changes in physical properties.

In a further embodiment of the third aspect of the present invention, the method further comprises the step of (v) isolating a nucleic acid from the mixture. Step (v) is preferably performed after the last step of the method as described above. Thus, if the method comprises step (i) and steps (ii), (iii), and (iv) are omitted, the nucleic acid is isolated from the mixture after step (i), if the method comprises steps (i) and (ii), the nucleic acid is isolated from the mixture after step (ii) etc. Most preferably, the beads which are optionally present in the mixture are removed before the mixture is applied to a nucleic acid isolation procedure. For example, the beads may be removed by letting the beads settle by gravity and transferring the supernatant to a fresh reaction tube. Most preferably, the mixture obtained after the last step of the method, i.e., step (i), (ii), (iii), or (iv), is suitable for being directly applied to a nucleic acid isolation procedure without the need for further processing such as extraction with organic solvents or precipitation before application to the nucleic acid isolation procedure. Thus, in a particularly preferred embodiment, the mixture is directly applied to a nucleic acid isolation procedure without any further processing such as extraction using organic solvents or precipitation before application to the nucleic acid isolation procedure. However, depending on the nucleic acid isolation procedure used it may be necessary to supplement the mixture with further reagents as described above, e.g., in the definitions and the second aspect of the present invention. The nucleic acid isolation procedure is preferably performed as described above, e.g., preferably using a silica-based or magnetic bead-based nucleic acid isolation technology, such as a nucleic acid isolation procedure based on silica membranes or silica beads, preferably based on silica membranes.

The method according to the third aspect of the present invention may comprise further steps, such as adjusting the pH, preferably neutralizing the mixture, for example, before step (ii) of the method. For example, the adjustment of the pH, preferably the neutralization of the mixture, may be performed using one or more buffering components, for example, as described above for the first aspect of the present invention.

In a particularly preferred embodiment of the third aspect of the present invention, the method comprises, preferably essentially consists of, preferably consists of the steps, preferably in this sequential order, (i) providing a mixture comprising the bodily sample to be processed, at least one chaotropic agent, at least one reducing agent, and at least one proteolytic enzyme, preferably providing a lysis reaction mixture as described above, optionally adjusting the pH preferably to about neutral or alkaline pH, (iv) optionally bead milling the mixture for 10 to 60 seconds, such as 30 seconds, preferably at about room temperature, (ii) incubating the mixture at 56±4° C. for at least 10 minutes, such as for 10, 12, 15, 20, or 25 minutes, optionally performing step (iv) bead milling for 10 to 60 seconds, such as for 30 seconds, at least once, preferably twice during previous step (ii), optionally (iv) bead milling the mixture for 10 to 60 seconds, such as 30 seconds, (iii) incubating the mixture at 96±5° C. for preferably 10 to 30 minutes, such as 15 minutes, optionally performing step (iv) bead milling for 10 to 60 seconds, such as for 30 seconds, at least once, preferably twice during previous step (iii), and (iv) bead milling the mixture, preferably using a bead miller, for 2 to 10 minutes, such as for 2, 3, 4, 5, 6, 7, 8, 9, or 10 minutes, preferably for 5 minutes, preferably during previous step (iii), preferably starting at the beginning of step (iii), or at about room temperature after previous step (iii). Preferably, the steps are preformed in an automated process starting with the step of mixing the components of the mixture in step (i).

In a fourth aspect, the present invention provides a method for analyzing a bodily sample comprising processing the bodily sample according to the method of the third aspect of the present invention and (vi) applying the mixture to a nucleic acid amplification/analysis method. Preferably, the mixture in this context is the considerably lysed, preferably fully lysed bodily sample, more preferably the mixture in this context is the eluate obtained from the nucleic acid isolation procedure (v). Preferably, the mixture refers to the mixture obtained in the last step of the method according to the third aspect of the present invention.

In a fifth aspect, the present invention provides a method for detecting the presence of a pathogen in a bodily sample comprising processing the bodily sample according to the method of the third aspect of the present invention and (vi) applying the mixture to a nucleic acid amplification/analysis method that is suitable for detection of said pathogen. Preferably, the mixture in this context is the considerably lysed, preferably fully lysed bodily sample, more preferably the mixture in this context is the eluate obtained from the nucleic acid isolation procedure (v). Preferably, the mixture refers to the mixture obtained in the last step of the method according to the third aspect of the present invention.

If the pathogen is a bacterium, the bacterium is preferably of a family selected from the group consisting of Mycobacteriaceae, Pseudomonadaceae, Mycoplasmataceae, Chlamydiaceae, Enterobacteriaceae, Staphylococcaceae, Streptococcaceae, Xantomonadaceae, Moraxellaceae, Legionellaceae, Burkholderiaceae, Corynebacteriaceae, Neisseriaceae, Bacteroides, and Pasteurellaceae. If the pathogen is a yeast, the yeast is preferably of a family selected from the group consisting of Saccharomycetaceae, Sporidiobolaceae, Trichocomaceae, and Pneumocystidaceae. Furthermore, also mycobacteria that are not associated with a disease may be detected using the method according to the fifth aspect of the present invention. The following species of the family Mycobacteriaceae may be detected using the method according to the fifth aspect of the present invention: *M. abscessus, M. africanum, M. agr, M. aichiense, M. alvei, M. arosiense, M. arupense, M. asiaticum, M. aubagnense, M. aurum, M. austroafricanum, Mycobacterium avium* complex (MAC) (group of species which are a significant cause of death in AIDS patients; species in this complex include: *M. avium, M. avium* paratuberculosis, which has been implicated in Crohn's disease in humans and Johne's disease in sheep, *M. avium silvaticum, M. avium* "hominissuis", *M. colombiense*), *M. boenickei, M. bohemicum, M. bolletii, M. botniense, M. bovis, M. branderi, M. brisbanense, M. brumae, M. canariasense, M. caprae, M. celatum, M. chelonae, M. chimaera, M. chitae, M. chlorophenolicum, M. chubuense, M. conceptionense, M. confluentis, M. conspicuum, M. cookii, M. cosmeticum, M. diernhoferi, M. doricum, M. duvalii, M. elephantis, M. fallax, M. farcinogenes, M. flavescens, M. florentinum, M. fluoroanthenivorans, M. fortuitum, M. fortuitum* subsp. *acetamidolyticum, M. frederiksbergense, M. gadium, M. gastri, M. genavense, M. gilvum, M. goodii, M. gordonae, M. haemophilum, M. hassiacum, M. heckeshornense, M. heidelbergense, M. hiberniae, M. hodleri, M. holsaticum, M. houstonense, M. immunogenum, M. interjectum, M. intermedium, M. intracellulare, M. kansasii, M. komossense, M. kubicae, M. kumamotonense, M. lacus, M. lentiflavum, M. leprae* (which causes leprosy), *M. lepraemurium, M. madagascariense, M. mageritense, M. malmoense, M. marinum, M. massiliense, M. microti, M. monacense, M. montefiorense, M. moriokaense, M. mucogenicum, M. murale, M. nebraskense, M. neoaurum, M. neworleansense, M. nonchromogenicum, M. novocastrense, M. obuense, M. palustre, M. parafortuitum, M. parascrofulaceum, M. parmense, M. peregrinum, M. phlei, M. phocaicum, M. pinnipedii, M. porcinum, M. poriferae, M. pseudoshottsii, M. pulveris, M. psychrotolerans, M. pyrenivorans, M. rhodesiae, M. saskatchewanense, M. scrofulaceum, M. senegalense, M. seoulense, M. septicum, M. shimoidei, M. shottsii, M. simiae, M. smegmatis, M. sphagni, M. szulgai, M. terrae, M. thermoresistibile, M. tokaiense, M. triplex, M. triviale, Mycobacterium tuberculosis* complex (MTBC) (members are causative agents of human and animal tuberculosis; species in this complex include: *M. tuberculosis*, the major cause of human tuberculosis, *M. bovis, M. bovis* BCG, *M. africanum, M. canetti, M. caprae, M. pinnipedii), M. tusciae, M. ulcerans*, which causes the "Buruli", or "Bairnsdale, ulcer", *M. vaccae, M. vanbaalenii, M. wolinskyi*, and *M. xenopi*.

Preferably, the bacterium of the family of Mycobacteriaceae is selected from the group consisting of *Mycobacterium tuberculosis, Mycobacterium bovis, Mycobacterium africanum, Mycobacterium canetti, Mycobacterium caprae, Mycobacterium smegmatis*, and *Mycobacterium pinnipedii*, the bacterium of the family of Pseudomonadaceae is *Pseudomonas aeruginosa*, the bacterium of the family of Mycoplasmataceae is *Mycoplasma pneumoniae*, the bacterium of the family of Chlamydiaceae is *Chlamydophila pneumoniae*, the bacterium of the family of Enterobacteriaceae is selected from the group consisting of *Citrobacter freundii, Citrobacter koseri, Enterobacter aerogenes, Enterobacter cloaceae, Enterobacter sakazakii, Klebsiella pneumoniae, Klebsiella oxytoca, Escherichia coli, Morganella morganii, Proteus mirabilis, Proteus vulgaris, Proteus penneri, Salmonella enterica, Serratia marcescens*, and *Yersinia pseudotuberculosis*, the bacterium of the family of Pasteurellaceae is selected from the group consisting of *Haemophilus influenzae* and *Haemophilus parainfluenzae*, the bacterium of the family of Staphylococcaceae is selected from the group consisting of *Staphylococcus aureus, Staphylococcus epidermis* and other coagulase-negative staphylococci (apathogenic host flora: *Gemella haemolysans, Gemella morbillorum*), the bacterium of the family of Streptococcaceae is selected from the group consisting of *Streptococcus pneumoniae, Streptococcus pyogenes*, and *Streptococcus agalactiae* (apathogenic host flora: *Streptococcus salivarius, Streptococcus mitis, Streptococcus oralis*, and *Streptococcus sanguinans*), the bacterium of the family Xanthomonadaceae is *Stenotrophomonas maltophilia*, the bacterium of the family of Moraxellaceae is selected from the group consisting of *Moraxella catarrhalis, Acinetobacter baumannii, Acinetobacter calcoaceticus* (flora), and *Acinetobacter lwoffii*, the bacterium of the family of Legionellaceae is *Legionella pneumophila*, the bacterium of the family Burkholderiaceae is *Burkholderia cepacia*, the bacterium of the family Corynebacteriaceae is *Corynebacterium diphtheriae*, the bacterium of the family Neisseriaceae is selected from the group consisting of *Neisseria meningitis, Neisseria flavescens*, and *Neisseria sicca*, and the bacterium of the family of Bacteroides is *Bacteroides fragilis*.

Preferably, the yeast of the family Saccharomycetaceae is selected from the group consisting of *Candida albicans, Candida dubliniensis, Candida glabrata, Candida krusei, Candida lusitania, Candida parapsilosis*, and *Candida tropicalis*, the yeast of the family Sporidiobolaceae is *Cryptococcus neoformans*, the yeast of the family Trichocomaceae is selected from the group consisting of *Aspergillus flavus* and *Aspergillus fumigatus*, and the yeast of the family Pneumocystidaceae is *Pneumocystis jirovecii*.

In a preferred embodiment of the fourth and fifth aspect of the present invention, the nucleic acid amplification/analysis method is selected from the group consisting of polymerase chain reaction (PCR), nucleic acid sequence-based amplification (NASBA), ligase chain reaction (LCR), strand displacement amplification (SDA), Q-beta replicase amplification, loop mediated isothermal amplification, multiple displacement amplification (MDA), and microarray analysis. However, it is noted that any other nucleic acid amplification/analysis method may be applied in the context of the present invention. Based on the general knowledge and the literature in the field, the skilled person is well aware of nucleic acid amplification/analysis methods and how to perform such methods. In a particular preferred embodiment, the nucleic acid amplification/analysis method is PCR.

Most preferably, the nucleic acid amplification procedure in the context of the fourth and fifth aspects of the present invention is suitable to detect, even more preferably to identify, the pathogen, wherein the pathogen is preferably a bacterium or yeast as described above. For example, the nucleic acid contained in the mixture, lysate, or eluate obtained by the method according to the third aspect of the present invention may be amplified by PCR using primers that are specific for the pathogen to be detected, e.g., the *mycobacterium*. The skilled person is well aware of how to design such specific primers based on the sequence of the pathogen genome which is generally publicly available, for example, on the National Center for Biotechnology Information (NCBI) homepage (http://www.ncbi.nlm.nih.gov).

A sixth aspect of the present invention relates to a method for diagnosing a respiratory disease in a subject comprising processing a bodily sample according to the method of the third aspect of the present invention and (vi) applying the mixture to a method that is suitable for diagnosing the respiratory disease. Preferably, the mixture in this context is the considerably lysed, preferably fully lysed bodily sample, more preferably the mixture in this context is the eluate obtained from the nucleic acid isolation procedure. Preferably, the mixture refers to the mixture obtained in the last step of the method according to the third aspect of the present invention. Preferably, the bodily sample is relevant for the diagnosis of a respiratory disease. Preferably, the respiratory disease is an infectious respiratory disease or a respiratory tumor. Preferably the respiratory disease is due to a viral, bacterial, fungal, or yeast infection, or is a respiratory tumor. Preferably the respiratory disease is as defined above, preferably selected from the group consisting of pneumonia, tuberculosis, bronchitis, pathogenic infections during cystic fibrosis or chronic obstructive pulmonary disease (COPD), and respiratory tumors.

A method that is suitable for diagnosing the respiratory disease in this context is preferably a molecular diagnostics method, preferably a nucleic acid amplification/analysis method, preferably as described above. For example, respiratory tract infections may be detected or diagnosed by detecting, preferably identifying the infecting pathogen, and respiratory tract tumors may be detected or diagnosed by detecting certain tumor associated antigens in the lysed bodily samples. For example, the method according to the sixth aspect may comprise the method according to the fourth or fifth aspect of the present invention. Thus, for example, the method for detecting the presence of a pathogen in a bodily sample according to the fifth aspect of the present invention may be used for diagnosing a respiratory disease, in particular, an infectious respiratory disease, according to the sixth aspect of the present invention.

Further aspects of the present invention provide a method for processing at least two bodily samples, such as 2, 3, 4, 5, 6, 7, 8, 9, 10, 20, 30, 50, 60, 70, 80, 90, or more than 100 bodily samples, comprising processing each of the at least two bodily samples according to the method of the third aspect of the present invention, wherein the at least two bodily samples are preferably different types of bodily samples, a method for analyzing at least two bodily samples, such as 2, 3, 4, 5, 6, 7, 8, 9, 10, 20, 30, 50, 60, 70, 80, 90, or more than 100 bodily samples, comprising analyzing each of the at least two bodily samples according to the method of the fourth aspect of the present invention, wherein the at least two bodily samples are preferably different types of bodily samples, and a method for detecting the presence of a pathogen in at least two bodily samples, such as 2, 3, 4, 5, 6, 7, 8, 9, 10, 20, 30, 50, 60, 70, 80, 90, or more than 100 bodily samples, comprising detecting the presence of a pathogen in each of the at least two bodily samples according to the method of the fifth aspect of the present invention, wherein the at least two bodily samples are preferably different types of bodily samples. Preferably, the at least two bodily samples are processed using a similar, preferably the identical embodiment of the method according to the third, fourth, or fifth aspect of the present invention. Preferably the methods according to these aspects are performed in a high-throughput setting.

The present invention further provides a method for processing a broad spectrum of bodily samples comprising processing each of the broad spectrum of bodily samples according to the method of the third aspect of the present invention, a method for analyzing a broad spectrum of bodily samples comprising analyzing each of the broad spectrum of bodily samples according to the method of the fourth aspect of the present invention, and a method for detecting the presence of a pathogen in a broad spectrum of bodily samples comprising detecting the presence of a pathogen in each of the broad spectrum of bodily samples according to the method of the fifth aspect of the present invention. Preferably, the bodily samples of the broad spectrum of bodily samples are processed using a similar, preferably the identical embodiment of the method according to the third, fourth, or fifth aspect of the present invention. Preferably the methods according to these aspects are performed in a high-throughput setting.

In another aspect, the present invention provides a lysate of a bodily sample comprising a bodily sample, preferably a bodily sample that is suitable for the diagnosis of a respiratory disease, at least one chaotropic agent, at least one reducing agent, and at least one proteolytic enzyme. Preferably, the components of the lysate are as described above, e.g., in the definitions and the first aspect of the present invention. Preferably, "bodily sample" in the context of the lysate according to the present invention means "the components of a bodily sample". Thus, "a lysate of a bodily sample comprising a bodily sample" preferably means "a lysate of a bodily sample comprising the components of a bodily sample".

In one embodiment, the lysate according to the present invention comprises a bodily sample, preferably as described above, and the lysis buffer according to the first aspect of the present invention. In one embodiment, the lysate according to the present invention is the lysis reaction mixture as described above, wherein preferably, the bodily sample is disintegrated, e.g., liquefied, preferably lysed.

The respiratory disease is preferably due to a viral, bacterial, fungal, or yeast infection. Preferably, the respiratory disease is as described above, and is preferably selected from the group consisting of pneumonia, tuberculosis, bronchitis, pathogenic infections during cystic fibrosis or chronic obstructive pulmonary disease (COPD), and respiratory tumors. Preferably, the bodily sample is untreated before contacting it with the other components of the lysate.

In one embodiment, the lysate is prepared by or is obtainable by mixing the sample and the lysis buffer according to the present invention in a volume ratio of sample to lysis buffer in the range of 0.5:1 to 1:2, e.g., in a ratio of 0.5:1, 0.6:1, 0.7:1, 0.8:1, 0.9:1, 1:1, 1:1.2, 1:1.4, 1:1.6, 1:1.8, or 1:2, preferably 1:1.2, wherein, if the lysis buffer contains beads, the volume of the lysis buffer is determined without the volume of the beads. In a preferred embodiment, the lysate is without beads, for example, because the lysis buffer did not contain beads or the beads have been removed from the lysate. Preferably, for producing the lysate the mixture of bodily sample is heated and/or bead milled, preferably heated and bead milled as described above for the third aspect of the present invention.

Furthermore, the lysate may also be prepared or is obtainable by adding the bodily sample to one or more components of the lysis buffer and then adding the optionally remaining component(s) of the lysis buffer. For example, the lysate may be prepared or may be obtainable by adding the bodily sample to a composition comprising at least one chaotropic agent and at least one reducing agent, preferably to the pre-mixed lysis composition as described above, and then adding the remaining components of the lysate, e.g., the proteolytic enzyme.

Furthermore, the present invention provides a lysate obtainable by processing a bodily sample according to the method of the third aspect of the present invention. Furthermore, the present invention provides a lysate obtainable by applying the use according to the second aspect of the present invention.

In another aspect, the present invention provides a kit comprising (i) a chaotropic agent, (ii) a reducing agent, (iii) a proteolytic enzyme, and (iv) an instruction leaflet, preferably an instruction leaflet for processing a bodily sample, preferably an instruction leaflet for lysing a bodily sample. Preferably, the components of the kit are as described above, e.g., in the definitions and the first aspect of the present invention. Preferably, the bodily sample is relevant for the diagnosis of a respiratory disease, preferably as described above. Preferably, the kit further comprises beads, preferably made of a solid inert material such as glass, ceramics, plastics, or metal such as steel, preferably as described above.

In a preferred embodiment of the kit according to the present invention, two or more components of the kit, for example, the chaotropic agent and the reducing agent, are provided in a composition. Preferably, the composition is provided in one or more reaction tubes, preferably ready-to-use reaction tubes. Preferably, said one or more reaction tubes comprise an aliquot of said composition which is suitable for the lysis of one bodily sample. Preferably, the volume of said aliquot is between ½ to ¹⁄₁₀, preferably ¼ to ¹⁄₁₀ of the volume of the reaction tube, such as ½, ⅓, ¼, ⅕, ⅙, ⅐, ⅛, ⅑, or ¹⁄₁₀ of the volume of the reaction tube. Said composition may comprise components other than the reducing agent and the chaotropic agent, such as a buffering component, for example, as described above for the first aspect of the present invention. Preferably, said composition does not comprise the proteolytic enzyme. It is preferred that the one or more reaction tubes also comprise the beads. Preferably, said composition is the pre-mixed lysis composition as described above in the definitions. Preferably, the one or more reaction tubes are screw cap tubes, preferably having a volume in the range of 0.2 to 50 ml, preferably, 0.2 to 15 ml, preferably 0.5 to 10 ml, preferably 1 to 2 ml, preferably 1.5 ml. The one or more reaction tubes may also be multiple-well format reaction vessels, such as strips of 8 or 12 reaction vessels or plates of 24, 48, or 96 reaction vessels, preferably having a firmly closeable lid. The nature and concentration of the components of the kit are preferably as defined above, e.g., in the definitions and for the components of the lysis buffer according to the first aspect of the present invention.

In a preferred embodiment of the kit according to the present invention, the proteolytic enzyme is provided separately from the chaotropic agent and the reducing agent, for example, the proteolytic enzyme may be provided in the kit in a separate storage tube. Alternatively, the proteolytic enzyme may be provided within the one or more reaction tubes comprising the composition, preferably the pre-mixed lysis composition, for example, in a dried spot in the lid of the tube, e.g., in the screw cap lid.

In a preferred embodiment, the kit further comprises means for DNA isolation, preferably a silica-based or magnetic bead-based nucleic acid isolation matrix, preferably as described above.

In a preferred embodiment, the kit according to the present invention is for lysis of a bodily sample, preferably as described above. In this embodiment, the kit may contain an instruction leaflet describing the method according to the third aspect of the present invention. In another preferred embodiment, the kit according to the present invention is for analysis of a bodily sample, preferably as described above. In this embodiment, the kit may contain an instruction leaflet describing the method according to the fourth aspect of the present invention. In another preferred embodiment, the kit according to the present invention is for detecting the presence of a pathogen in a bodily sample, preferably as described above. In this embodiment, the kit may further comprise means for detection of a pathogen, for example, oligonucleotides, such as primers or probes, specific for the nucleic acid derived from said pathogen. In this embodiment, the kit may contain an instruction leaflet describing the method according to the fifth aspect of the present invention.

In another preferred embodiment, the kit according to the present invention is for lysis of a broad spectrum of bodily samples, preferably for lysis of at least 2, preferably at least 3, preferably at least 4, preferably at least 5, preferably at least 6, preferably at least 7 different types of bodily samples, preferably as described above. In another preferred embodiment, the kit according to the present invention is for analysis of a broad spectrum of bodily samples, preferably for analysis of at least 2, preferably at least 3, preferably at least 4, preferably at least 5, preferably at least 6, preferably at least 7 different types of bodily samples, preferably as described above. In another preferred embodiment, the kit according to the present invention is for detecting the presence of a pathogen in a broad spectrum of bodily samples, preferably for detecting the presence of a pathogen in at least 2, preferably at least 3, preferably at least 4, preferably at least 5, preferably at least 6, preferably at least 7 different types of bodily samples, preferably as described above. In this embodiment, the kit may further comprise means for detection of a pathogen, for example, oligonucleotides, such as primers or probes, specific for the nucleic acid derived from said pathogen. Preferably, the bodily samples are relevant for the diagnosis of a respiratory disease.

In another embodiment, the kit is for diagnosis of a respiratory disease, preferably by molecular diagnostics, preferably by nucleic acid analysis, for example, by detecting and/or identifying pathogens or a respiratory tumor marker, as described above. In this embodiment, the kit preferably further comprises means for detection of a pathogen or a respiratory tumor marker, for example, oligonucleotides, such as primers or probes, specific for the nucleic acid derived from said pathogen or for the respiratory tumor marker. In this embodiment, the kit preferably further comprises an instruction leaflet describing the method according to the sixth aspect of the present invention.

Preferably, the kit according to the present invention is universally applicable to the lysis of bodily samples, preferably bodily samples relevant for the diagnosis of a respiratory disease.

In preferred embodiments, the kit according to the present invention is for performing the method according to the third aspect of the present invention, the method according to the fourth aspect of the present invention, the method according to the fifth aspect of the present invention, or the method according to the sixth aspect of the present invention.

The present invention provides for the first time a lysis buffer, a use, a processing method, and a kit which are universally applicable to the lysis of bodily samples. This allows for the first time to perform the lysis of several types of different bodily samples, such as bodily samples relevant for the diagnosis of a respiratory disease, in parallel using the same lysis buffer and processing protocol, and thus, to process different types of bodily samples in a high-throughput setting. Furthermore, the present invention provides a valuable alternative to existing approaches for the processing, preferably the lysis of bodily samples, in particular such bodily samples which are difficult to handle, e.g., respiratory samples such as sputum or tracheal secretions, especially if isolation of nucleic acids and subsequent analysis thereof is required. Some of the advantages of the present invention are a low infection risk, especially if highly pathogenic organisms are to be detected, efficient solubilization/liquefaction and/or lysis of highly viscous samples, reduced handling, possibility for automating the process and performing the process in a high-throughput setting even for different sample types, and compatibility to different DNA isolation methods.

EXAMPLES

The following examples serve to illustrate particularly preferred embodiments of the present invention and are not to be construed as limiting the scope of the invention in any manner. Those skilled in the art will recognize that various modifications may be made to the foregoing description and the following examples without departing from the spirit and scope of the invention.

Example 1

Process Details and Overview

| Materials and Equipment | | |
|---|---|---|
| consumables and chemicals | | |
| item | supplier | ordering number |
| screw cap tubes (1.5 ml) | e.g., neolab | 1-6186 |
| screw caps | e.g., neolab | 1-6193 |
| glass beads, 425-600 µm, acid-washed | Sigma-Aldrich | G8772 |
| lysis buffer AL | Qiagen | 19075 |
| DL-Dithiothreitol (DTT) solution 1M | Sigma-Aldrich | 43816 |
| Proteinase K (20 mg/ml, >600 mAU/ml) | Qiagen (ready-to-use solution) alternatively Sigma-Aldrich (solid) | 19131 P2308 |

| Materials and Equipment | | |
|---|---|---|
| ethanol 96% | Carl Roth | P075.3 |
| QiaAmp ™ Blood Mini Kit | Qiagen | 51104 |
| Eppendorf Dualfilter T.I.P.S. (50-1000 µl) | neolab | E6513 |
| equipment | | |
| item | supplier | comment |
| heating block (56-96° C.) | e.g., Eppendorf thermomixer | or equivalent |
| bead milling device | Curetis | |
| vortex mixer | e.g., IKA | or equivalent |
| centrifuge (13000 rpm) | e.g., Heraeus Biofuge fresco | or equivalent |
| composition of lysis tube | | |
| item | amount/concentration | |
| glass beads, 600 µm, acid-washed | 140 mg | |
| lysis buffer AL | 230 µl | |
| DTT solution 1M | 10 µl | |
| Proteinase K | 20 µl (added together with sample) | |
| patient sample | 220 µl | |
| total volume (final reaction) | 480 µl | |

Preparation and Storage of Lysis Tubes (Ready-To-Use Reaction Tubes)

Lysis tubes contain 140 mg+/−20 mg glass beads, 230 µl+/−5 µl lysis buffer AL, 10 µl+/−2 µl 1 M DTT. The tubes are stored at a temperature between 15 and 25° C. Proteinase K is stored separately without contact to buffer AL between 15 and 25° C. either in liquid form or as dried spot (e.g., on the inside of a screw cap).

Process Overview

The method according to the present invention may be performed either manually using standard lab equipment like mixers (vortex) and heating blocks or automated using an automated device such as a bead miller. Examples for a manual and an automated process according to the present invention are provided in FIGS. 1 and 2, respectively.

Most preferably, for best efficiencies and reduced process times, the process is performed using a bead milling device, which is capable of performing agitation, such as rotation about several axes, and heating steps simultaneously, which allows full automation of the processing method according to the present invention.

Process example A (FIG. 1) is a manual process using a standard vortex for mixing at 2500 rpm (standard maximum speed for an IKA vortex, devices from other suppliers might vary) for 30 sec (other times might work as well), pre-heated heating blocks and a bead milling device capable of a milling speed relating to approx. 100 g (other speeds might work as well, and speed may vary for other devices with different geometry). Note that for all milling/mixings steps the tubes were removed from the heating block and processed at room temperature.

Process example B (FIG. 2) is an automated process using a bead milling device which performs all process steps. Milling speeds relate to forces between 50-100 g dependent on the device geometries. As the tubes are heated together with the chambers to the target temperatures longer ramping rates are included in this example, still, ramping times are not critical and may also be considerably shorter.

Method Steps
Sample Input

Sample volume was 220 µl+/−10 µl. After adding the sample and proteinase K to the lysis tube, the tube was mixed vigorously either using a vortex or bead miller at high speed (up to 100 g) for up to 1 minute to ensure good homogenization of sample and lysis buffer. The addition of the sample was performed under a laminar flow. If infection with *Mycobacterium tuberculosis* complex was suspected all work until the 96° C. heating step has been performed within an S3 laboratory. In general, also filter tips were used for pipetting to avoid cross-contamination of samples. Use of slant-cut filter tips with widened opening is recommended for pipetting aliquots from highly viscous samples.

Heating Steps

The first heating step was performed at 56° C.+/−1° C. for 10 minutes for proteinase K digestion. The second heating step was performed at 96° C.+/−1° C. for 15 min for thermal lysis. This step is preferably not reduced below 5 minutes to assure complete liquefaction. If this step is performed to reduce the infection risk, legal requirements may be applicable in different clinical settings for minimum heating duration. During and between 56° C. and 96° C. incubation steps the tubes may be shortly mixed or milled for up to 1 minute at various speeds to resolve any unliquefied sample bits.

Bead Milling

Bead milling was performed with a bead milling device capable of parallel milling and heating. Alternatively, the sample may be processed manually by vigorous mixing using a vortex. Short milling steps may be performed throughout the entire protocol either manually using a vortex or using the bead milling device with 50-100 g. A final milling step was either performed at room temperature for several minutes (5 minutes) after completing the 96° C. heating step or, preferably, for improved lysis efficiencies and reduced process times, during the 96° C. heating step with a force of up to 100 g and a milling time of several minutes (5 minutes) using the bead milling device. If incubation time at 96° C. exceeded the milling time another short milling step was performed at the end of the process.

Process Finalization

Lysis tubes were cooled down to a reasonable temperature after the process has finished to prevent any hazards (burns) to the user when removing the tube from the lysator.

Supernatant Transfer and DNA Purification

Filter tips have been used for all pipetting steps. 400 µl+/−10 µl liquefied supernatant were transferred into a fresh 1.5 ml screw cap tube. 200 µl+/−10 µl 96% ethanol were added to the supernatant and the tube was shortly mixed. The mixture (approx. 600 µl) was loaded onto a silica membrane column (QiaAmp™) and processed either by centrifugation or by vacuum of up to −800 mbar according to the manufacturer's recommendations.

Full Lysis Protocol

Ready-to-use lysis tubes containing all necessary reagents and Proteinase K (either liquid or dried) have been stored at room temperature. Fresh patient samples were collected according to clinical standard procedures. An aliquot of the sample (220 µl) was transferred to a lysis tube. Proteinase K (20 µl) was added and the screw cap of the lysis tube was tightly closed. For transfer of mucous sample aliquots slant-cut 1000 µl pipette tips were used.

For the manual process, the tube was shortly mixed by vortexing to assure optimal contact of lysis buffer to sample, in particular, for highly viscous specimens. The tube was then placed into a heating block (56° C.) for 10 minutes for optimal proteinase K digest. After the digest, the tube was shortly mixed and transferred to a heating block (96° C.) for a second heating step of 15 minutes. Once or twice during both heating steps the sample may be taken out, shortly vortexed, and transferred back to the heating block. After the 96° C. heating step had been completed, the sample was transferred to a bead milling device (alternatively, a vortex can be used) and bead milling was performed for 5 minutes (up to 100 g) to resolve any unlysed sample particles. After all lysis steps had been completed, 400 µl of the liquefied supernatant were transferred to a new screw cap tube.

For the automated process, the lysis tube was placed into the bead milling device immediately after sample and proteinase K addition, and the lysis process was started without any further handling or mixing requirements for the user (FIG. 2). After the process had been completed, the tubes containing the lysed samples were removed from the device and supernatants were transferred as described.

For QiaAmp™ DNA purification, 200 µl ethanol (96%) were added to the transferred supernatant. After short mixing, the lysate was transferred to a QiaAmp™ spin column (Qiagen). Further purification steps were performed according to the manufacturer's recommendations. DNA was eluted with 200 µl pure water.

Example 2

Sample Type Variability and Impact of Lysis Features 76 samples of different origins (respiratory and relevant other samples, like punctates and drainages) were scored for viscosity, blood and sediment content to describe the differences of sample types based on the average score (FIG. 3). Included number of samples for each type are given in brackets. From each sample type, including blood, reference samples were selected to cover the full range of relevant samples for respiratory diseases (total: 12 samples).

Each of these samples was subjected to three different lysis protocols to determine the impact of individual lysis features: (a) manual full protocol as described above, (b) full protocol without addition of proteinase K, (c) protocol without 96° C. heating step (instead sample was placed to ambient temperature). All samples have been subjected to a final bead milling step of 5 minutes, the lysate was then transferred, mixed with ethanol and applied to a silica membrane column as described. Lysis efficiencies were scored after proteinase K digest (first heating step), 96° C. heating step, and bead milling, and lysis efficiencies were determined.

The flow through silica membranes was monitored using a centrifuge at reduced speed (4000 rpm instead of recommended 8000 rpm), after application of the entire sample volume, the membranes were checked for coloring or remaining sample components which might indicate insufficient lysis (FIG. 4). Two samples resulted in slightly colored membranes, however, this did not have any impact on flow-through. Unlysed sample bits have not been detected on the silica membranes. For another sample a slight colorization and some flow restriction was detected, although lysis was complete. FIG. 5 shows typical examples of successfully lysed patient samples using the processing method of the present invention (A/B: sputa, C: tracheal secretion).

Example 3

Lysis Efficiency and Flow Behavior Through Silica Membranes without Proteinase K Treatment In a second set of experiments, the impact of the proteinase K digestion, heating, milling and parallel heating/milling was examined with tracheal secretions. In particular, samples with high viscosities and/or sediment have been selected. Such samples are likely to be difficult to lyse. In a first step, the samples were incubated at 96° C. for 15 min directly after addition to the lysis buffer (without proteinase K) and short mixing. Bead milling was either performed for 5 min at room temperature after completion of the 96° C. incubation step [M] or parallel to the heating step. The progress of the lysis was monitored over time. Lysed supernatants were then mixed with ethanol and applied to silica membranes as described above. Flow-through was monitored at increasing centrifugal forces starting at 4000 rpm. FIGS. 6A and 6B each show two examples reflecting the observed variability for different samples.

Several samples displayed flow-restrictions although lysis seemed to be sufficient by visual observation. Sometimes a slight turbidity was visible which did not correlate to reduced flows. One sample (tracheal secretion 1) failed to lyse completely when no parallel milling at 96° C. was performed.

Parallel milling during the 96° C. incubation step decreased the time required for full lysis and had a significant effect on process speed and lysis success.

Example 4

Lysis Efficiency and Flow Behavior Through Silica Membranes with Proteinase K Treatment A proteinase K digestion step was included (56° C. for 10 minutes) and aliquots of the same samples as used for Example 3 were lysed and monitored as described for Example 3.

Some samples were already lysed during the proteinase K digestion step, whereas others did not change by proteinase K digestion. Occurrence of turbidity was reduced and flow-through was now greatly improved. Certain samples which required higher centrifugal forces when lysed without the proteinase K digestion step performed now very well already at low centrifugal forces. Unlysed residual sample has not been observed any more (FIG. 7).

Thus, the proteinase K digestion step is advantageous for the lysis of bodily samples, for example, for sputa or secretions, in particular, if a nucleic acid isolation procedure using low centrifugal forces or a vacuum-based system is intended. As in Example 3, parallel milling during heating showed a clear increase in lysis efficiency and reduction of process time.

Example 5

DNA Quality and PCR Performance with Different Sample Types

Seven patient samples of different origins were spiked with *Pseudomonas aeruginosa* (20000 pathogens/ml=4400 pathogens/220 µl used sample) and lysed using the manual protocol as described above in Example 1 and shown in FIG. 1. DNA was isolated with the QiaAmp™ DNA Blood Kit using a centrifuge. The quality of the DNA which was isolated from the spiked patient samples was monitored by spectral analysis of the 5-fold diluted eluate (220-320 nm) (FIG. 8).

Putative co-purification of PCR inhibitors was checked by a PCR inhibition test. In short, 3 µl of 200 µl eluate were added to PCRs, which produce, in absence of any inhibitory effect, 3 amplicons of different size with a known average molarity. For inhibition tests, molarities generated in presence of the DNA eluates were compared to 4 control PCRs (eluates generated from phosphate buffered saline)

Furthermore, a *P. aeruginosa* PCR was performed and amplicon molarities and DNA yields of eluates were compared (FIG. 10).

All spectra show the typical appearance of pure DNA. Furthermore, no inhibition was visible compared to controls. The DNA yield, however, varies strongly, reflecting the background DNA level of individual samples. Still the level of *P. aeruginosa* amplification was in a comparable range, although there was some variability, in particular, for viscous samples which are difficult to mix with the pathogen suspensions during spiking.

Example 6

Pathogen Detection in Different Types of Bodily Patient Samples 27 patient samples were processed using the manual lysis protocol as described above in Example 1 and FIG. 1. Silica membrane purified DNA was analyzed using multiplex PCRs for detecting common respiratory pathogens (*Klebsiella pneumoniae, Streptococcus pneumoniae, Haemophilus influenzae, Staphylococcus aureus, Escherichia coli, Pseudomonas aeruginosa*, and *Streptococcus* species as indicator of host flora). In short, 3 µl DNA eluate were amplified with the Multiplex PCR Kit (Qiagen) together with multiplexed primers (350 nM final concentration each) in a total volume of 30 µl for 35 cycles. Amplicon molarities were determined using an Agilent Bioanalyzer (FIG. 11).

PCR results were compared with data obtained from microbiological culture tests for these samples (FIG. 12). For most of the samples, microbiological culture tests did not identify pathogens on a genus level, but rather detected cocci, rods, or respiratory (host) flora in general. Indeed, microbiological culture tests were able to identify a pathogen genus in only 5 samples, and all of them were confirmed by a positive PCR result. Note that the *Haemophilus* primers used in this test do not discriminate between the species *influenzae* and *parainfluenzae*. The results of these experiments clearly demonstrate that PCR allows for a much more sophisticated analysis and diagnosis of respiratory diseases by providing more differentiated information on the individual pathogens than microbiological culture tests.

Example 7

Performance of the Automated Lysis Protocol with Clinical Samples

A device for full automation of the lysis process has been developed and performance was tested applying "process example B" (FIG. 2) on clinical samples which have been tested positive with microbiological culture. The results were compared to the manual lysis protocol (FIG. 1). Tracheal secretions with high viscosities were selected for this test. DNA isolation from the lysates was performed using silica membranes as described above and triplex PCR was performed on eluates with *Pseudomonas-*, *Staphylococcus-* and *Candida-*specific primers (FIG. 13).

To exclude any effects of sample freezing and thawing for pathogen lysis, a second set of samples was spiked with *Pseudomonas aeruginosa* (gram-negative) and *Staphylococcus aureus* (gram-positive) at 20000 pathogens/ml and processed using the manual or the automated protocol (FIG. 14).

Both protocols, i.e., the manual and the automated protocol, succeeded in reproducing the results obtained by microbiological culture tests. Furthermore, spiked pathogens have been detected at comparable levels in all tests. Thus, the automated process is as efficient as the manual process.

The experimental data strongly supports that the present invention will facilitate molecular diagnostics for respiratory samples for a broad range of all relevant sample types by the use of a user-friendly standardized protocol. Lysis can be combined with nucleic acid isolation procedures, for example, using silica membranes, to obtain high-quality DNA for subsequent PCR. Such DNA can be used for fast and simultaneous detection of pathogens and risk factors in a much faster and more efficient way compared to standard microbiological culture. Pre-aliquoted lysis tubes reduce sample-to-sample variation, handling steps, and infection risk. The automated process allows for easy and uniform sample processing without the need for trained personnel and user interaction.

The invention claimed is:

1. A method for processing a highly viscous bodily sample, wherein the processing comprises liquefaction of said highly viscous bodily sample, said method comprising the steps of:
   (i) contacting a highly viscous bodily sample, wherein the highly viscous bodily sample has a viscosity of at least $1 \times 10^4$ mPa·s, with a combination comprising:
      at least one chaotropic agent,
      at least one reducing agent, and
      at least one proteolytic enzyme;
   (ii) forming a mixture comprising the highly viscous bodily sample and the combination,
   (iii) heating the mixture to a first temperature,
   (iv) heating the mixture to a second temperature, wherein the second temperature is higher than the first temperature, and
   (v) bead milling the mixture, wherein said bead milling is performed simultaneously to or during steps (iii) or (iv),
   thereby liquefying the highly viscous bodily sample.

2. A method for processing a highly viscous bodily sample, wherein the processing comprises liquefaction of said highly viscous bodily sample, said method comprising the steps of:
   (i) providing a mixture comprising the bodily sample to be processed, wherein the highly viscous bodily sample has a viscosity of at least $1 \times 10^4$ mPa·s, at least one chaotropic agent, at least one reducing agent, and at least one proteolytic enzyme, and
   (ii) heating the mixture to a first temperature,
   (iii) heating the mixture to a second temperature, wherein the second temperature is higher than the first temperature, and
   (iv) bead milling the mixture, wherein said bead milling is performed simultaneously to or during steps (ii) or (iii),
   thereby liquefying the highly viscous bodily sample.

3. The method according to claim 2, wherein steps (ii) to (iv) are performed in an automated process.

4. The method according to claim 2, further comprising the step of: (v) isolating a nucleic acid from the mixture.

5. A method for analyzing a highly viscous bodily sample comprising processing the highly viscous bodily sample according to the method of claim 2 and (v) applying the mixture to a nucleic acid amplification and/or analysis method.

6. A method for detecting the presence of a pathogen in a highly viscous bodily sample comprising processing the highly viscous bodily sample according to the method of claim 2 and (v) applying the mixture to a nucleic acid amplification and/or analysis method that is suitable for detection of said pathogen.

7. A method for processing at least two highly viscous bodily samples comprising processing each of the at least two highly viscous bodily samples according to the method of claim 2, wherein the at least two bodily samples are different types of bodily samples.

8. A method for processing a highly viscous bodily sample, wherein the processing comprises liquefaction of said highly viscous bodily sample, said method comprising the steps of:
   providing a mixture comprising the bodily sample to be processed, wherein the highly viscous bodily sample has a viscosity of at least $1 \times 10^4$ mPa·s, at least one chaotropic agent, at least one reducing agent, and at least one proteolytic enzyme,
   (ii) incubating said mixture,
   (iii) heating said mixture to a first temperature,
   (iv) heating said mixture to a second temperature, wherein the second temperature is higher than the first temperature, and
   (v) bead milling said mixture, wherein step (v) is performed simultaneously to or during step (iv), thereby liquefying the highly viscous bodily sample.

9. A method for diagnosing a respiratory disease in a subject comprising
   (i) providing a mixture comprising a highly viscous bodily sample to be processed, wherein the highly viscous bodily sample has a viscosity of at least $1 \times 10^4$ mPa·s, at least one chaotropic agent, at least one reducing agent, and at least one proteolytic enzyme,
   (ii) incubating said mixture,
   (iii) heating said mixture to a first temperature,
   (iv) heating said mixture to a second temperature, wherein the second temperature is higher than the first temperature, and
   (v) bead milling said mixture, wherein said bead milling is performed simultaneously to or during steps (iii) or (iv), thereby liquefying the highly viscous bodily sample, and
   (vi) applying the mixture to a method that is suitable for diagnosing the respiratory disease.

* * * * *

UNITED STATES PATENT AND TRADEMARK OFFICE
CERTIFICATE OF CORRECTION

| | | |
|---|---|---|
| PATENT NO. | : 9,598,721 B2 | Page 1 of 1 |
| APPLICATION NO. | : 13/698216 | |
| DATED | : March 21, 2017 | |
| INVENTOR(S) | : Matthias Klein et al. | |

It is certified that error appears in the above-identified patent and that said Letters Patent is hereby corrected as shown below:

On the Title Page

In the abstract, Line 2, "chaotropic 5" should be changed to --chaotropic--.
In the abstract, Line 18, "are 15 suitable" should be changed to --are suitable--.

In the Specification

Column 20, Line 17, "C." should be changed to --C--.
Column 20, Line 18, "C." should be changed to --C--.
Column 22, Line 42, "messenger." should be changed to --messenger,--.
Column 23, Line 58, "Acinetobacter Legionellaceae" should be changed to --Acinetobacter Iwoffii), Legionellaceae--.
Column 27, Line 28, "mAU/m" should be changed to --mAU/ml--.

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*